United States Patent
Otte et al.

(10) Patent No.: US 9,084,664 B2
(45) Date of Patent: Jul. 21, 2015

(54) METHOD AND ARTICLES FOR TREATMENT OF STRESS URINARY INCONTINENCE

(75) Inventors: John Fritz Otte, Minnetonka, MN (US);
Robert E. Lund, Minnetonka, MN (US);
John Jason Buysman, Minnetonka, MN (US); Edouard A. Koullick, Minnetonka, MN (US); Ross A. Longhini, Minnetonka, MN (US);
James B. Presthus, Minnetonka, MN (US)

(73) Assignee: AMS Research Corporation, Minnetonka, MN (US)

(*) Notice: Subject to any disclaimer, the term of this patent is extended or adjusted under 35 U.S.C. 154(b) by 1273 days.

(21) Appl. No.: 12/227,426

(22) PCT Filed: May 21, 2007

(86) PCT No.: PCT/US2007/069370
§ 371 (c)(1),
(2), (4) Date: Apr. 15, 2009

(87) PCT Pub. No.: WO2007/137226
PCT Pub. Date: Nov. 29, 2007

(65) Prior Publication Data
US 2010/0010631 A1   Jan. 14, 2010

Related U.S. Application Data

(60) Provisional application No. 60/747,736, filed on May 19, 2006, provisional application No. 60/819,370, filed on Jul. 10, 2006.

(51) Int. Cl.
*A61F 2/02* (2006.01)
*A61F 2/00* (2006.01)
(Continued)

(52) U.S. Cl.
CPC ............. *A61F 2/0045* (2013.01); *A61F 2/0036* (2013.01); *A61L 27/50* (2013.01); *A61L 31/14* (2013.01); *A61F 2/08* (2013.01)

(58) Field of Classification Search
USPC .......................................................... 600/30
See application file for complete search history.

(56) References Cited

U.S. PATENT DOCUMENTS

| 2,738,790 A | 3/1956 | Todt et al. |
| 3,054,406 A | 9/1962 | Usher |

(Continued)

FOREIGN PATENT DOCUMENTS

| AU | 2002241673 | 11/2005 |
| CA | 2404459 | 8/2005 |

(Continued)

OTHER PUBLICATIONS

"Access Instrument System with AlloSling Fascia" (5 pages with two pages of Instructions for Use).

(Continued)

*Primary Examiner* — Victoria J Hicks
(74) *Attorney, Agent, or Firm* — Kagan Binder, PLLC

(57) ABSTRACT

Improved methods and apparatuses for treatment of incontinence or pelvic organ prolapse are provided. A neo ligament for increasing the supportive function of the tissues supporting the urethra, bladder neck, or rectum is disclosed. Methods of using such a neoligament to treat incontinence are disclosed. Additionally, a self tensioning elastic tissue bolster for support of the tissues that support the urethra, rectum, and bladder neck are disclosed. A method of treating incontinence by injecting proliferative agents into supportive structures is disclosed. Methods and apparatus for transvaginal and transperineal pelvic floor bolster treatment of incontinence and bladder pillar systems are also disclosed.

8 Claims, 15 Drawing Sheets

(51) Int. Cl.
*A61L 27/50* (2006.01)
*A61L 31/14* (2006.01)
*A61F 2/08* (2006.01)

(56) References Cited

U.S. PATENT DOCUMENTS

| | | | |
|---|---|---|---|
| 3,124,136 A | 3/1964 | Usher | |
| 3,182,662 A | 5/1965 | Shirodkar | |
| 3,311,110 A | 3/1967 | Singerman et al. | |
| 3,384,073 A | 5/1968 | Van Winkle, Jr. | |
| 3,472,232 A | 10/1969 | Earl | |
| 3,580,313 A | 5/1971 | McKnight | |
| 3,763,860 A | 10/1973 | Clarke | |
| 3,789,828 A | 2/1974 | Schulte | |
| 3,815,576 A | 6/1974 | Balaban | |
| 3,858,783 A | 1/1975 | Kapitanov et al. | |
| 3,995,619 A | 12/1976 | Glatzer | |
| 4,019,499 A | 4/1977 | Fitzgerald | |
| 4,037,603 A | 7/1977 | Wendorff | |
| 4,128,100 A | 12/1978 | Wendorff | |
| 4,172,458 A | 10/1979 | Pereyra | |
| 4,235,238 A | 11/1980 | Ogiu et al. | |
| 4,441,497 A | 4/1984 | Paudler | |
| 4,509,516 A | 4/1985 | Richmond | |
| 4,548,202 A | 10/1985 | Duncan | |
| 4,632,100 A | 12/1986 | Somers et al. | |
| 4,775,380 A | 10/1988 | Seedhom et al. | |
| 4,857,041 A | 8/1989 | Annis et al. | |
| 4,865,031 A | 9/1989 | O'Keeffe | |
| 4,873,976 A | 10/1989 | Schreiber | |
| 4,920,986 A | 5/1990 | Biswas | |
| 4,932,962 A | 6/1990 | Yoon et al. | |
| 4,938,760 A | 7/1990 | Burton et al. | |
| 4,969,892 A | 11/1990 | Burton et al. | |
| 4,979,956 A | 12/1990 | Silvestrini | |
| 5,007,894 A | 4/1991 | Enhorning | |
| 5,012,822 A | 5/1991 | Schwarz | |
| 5,013,292 A | 5/1991 | Lemay | |
| 5,013,316 A | 5/1991 | Goble et al. | |
| 5,019,032 A | 5/1991 | Robertson | |
| 5,032,508 A | 7/1991 | Naughton et al. | |
| 5,036,867 A | 8/1991 | Biswas | |
| 5,053,043 A | 10/1991 | Gottesman et al. | |
| 5,085,661 A | 2/1992 | Moss | |
| 5,112,344 A | 5/1992 | Petros | |
| 5,123,428 A | 6/1992 | Schwarz | |
| 5,141,520 A | 8/1992 | Goble et al. | |
| 5,149,329 A | 9/1992 | Richardson | |
| 5,188,636 A | 2/1993 | Fedotov | |
| 5,209,756 A | 5/1993 | Seedhom et al. | |
| 5,234,438 A | 8/1993 | Semrad | |
| 5,242,391 A * | 9/1993 | Place et al. | 604/60 |
| 5,256,133 A | 10/1993 | Spitz | |
| 5,268,001 A | 12/1993 | Nicholson et al. | |
| 5,269,783 A | 12/1993 | Sander | |
| 5,281,237 A | 1/1994 | Gimpelson | |
| 5,328,077 A | 7/1994 | Lou | |
| 5,337,736 A | 8/1994 | Reddy | |
| 5,354,292 A | 10/1994 | Braeuer et al. | |
| 5,362,294 A | 11/1994 | Seitzinger | |
| 5,368,595 A | 11/1994 | Lewis | |
| 5,370,650 A | 12/1994 | Tovey et al. | |
| 5,370,662 A | 12/1994 | Stone et al. | |
| 5,376,097 A | 12/1994 | Phillips | |
| 5,383,904 A | 1/1995 | Totakura et al. | |
| 5,386,836 A | 2/1995 | Biswas | |
| 5,403,328 A | 4/1995 | Shallman | |
| 5,439,467 A | 8/1995 | Benderev et al. | |
| 5,474,518 A | 12/1995 | Velazquez | |
| 5,474,543 A | 12/1995 | McKay | |
| 5,518,504 A | 5/1996 | Polyak | |
| 5,520,700 A | 5/1996 | Beyar et al. | |
| 5,520,703 A | 5/1996 | Essig | |
| 5,527,342 A | 6/1996 | Pietrzak et al. | |
| 5,544,664 A | 8/1996 | Benderev et al. | |
| 5,562,689 A | 10/1996 | Green et al. | |
| 5,571,139 A | 11/1996 | Jenkins, Jr. | |
| 5,582,188 A | 12/1996 | Benderev et al. | |
| 5,591,163 A | 1/1997 | Thompson | |
| 5,591,206 A | 1/1997 | Moufarrege | |
| 5,611,515 A | 3/1997 | Benderev et al. | |
| 5,628,756 A | 5/1997 | Barker, Jr. et al. | |
| 5,643,320 A | 7/1997 | Lower et al. | |
| 5,669,935 A | 9/1997 | Rosenman et al. | |
| 5,683,349 A | 11/1997 | Makower et al. | |
| 5,690,655 A | 11/1997 | Hart et al. | |
| 5,697,931 A | 12/1997 | Thompson | |
| 5,709,708 A | 1/1998 | Thal | |
| 5,725,529 A | 3/1998 | Nicholson et al. | |
| 5,725,541 A | 3/1998 | Anspach, III et al. | |
| 5,741,282 A | 4/1998 | Anspach, III et al. | |
| 5,782,916 A | 7/1998 | Pintauro et al. | |
| 5,785,640 A | 7/1998 | Kresch et al. | |
| 5,807,403 A | 9/1998 | Beyar et al. | |
| 5,836,314 A | 11/1998 | Benderev et al. | |
| 5,836,315 A | 11/1998 | Benderev et al. | |
| 5,840,011 A | 11/1998 | Landgrebe et al. | |
| 5,842,478 A | 12/1998 | Benderev et al. | |
| 5,860,425 A | 1/1999 | Benderev et al. | |
| 5,899,909 A | 5/1999 | Claren et al. | |
| 5,904,692 A | 5/1999 | Steckel et al. | |
| 5,919,232 A | 7/1999 | Chaffringeon et al. | |
| 5,922,026 A | 7/1999 | Chin | |
| 5,925,047 A | 7/1999 | Errico et al. | |
| 5,934,283 A | 8/1999 | Willem et al. | |
| 5,944,732 A | 8/1999 | Raulerson et al. | |
| 5,954,057 A | 9/1999 | Li | |
| 5,972,000 A | 10/1999 | Beyar et al. | |
| 5,980,558 A | 11/1999 | Wiley | |
| 5,984,927 A | 11/1999 | Wenstrom, Jr. | |
| 5,988,171 A | 11/1999 | Sohn et al. | |
| 5,997,554 A | 12/1999 | Thompson | |
| 6,010,447 A | 1/2000 | Kardjian | |
| 6,027,523 A | 2/2000 | Schmieding | |
| 6,030,393 A | 2/2000 | Corlew | |
| 6,031,148 A | 2/2000 | Hayes et al. | |
| 6,036,701 A | 3/2000 | Rosenman | |
| 6,039,686 A | 3/2000 | Kovac | |
| 6,042,534 A * | 3/2000 | Gellman et al. | 600/30 |
| 6,042,536 A | 3/2000 | Tihon et al. | |
| 6,042,583 A | 3/2000 | Thompson et al. | |
| 6,048,351 A | 4/2000 | Gordon et al. | |
| 6,050,937 A | 4/2000 | Benderev | |
| 6,053,935 A | 4/2000 | Brenneman et al. | |
| 6,056,688 A | 5/2000 | Benderev et al. | |
| 6,068,591 A | 5/2000 | Bruckner et al. | |
| 6,074,341 A | 6/2000 | Anderson et al. | |
| 6,077,216 A | 6/2000 | Benderev et al. | |
| 6,099,538 A | 8/2000 | Moses | |
| 6,106,545 A | 8/2000 | Egan | |
| 6,110,101 A | 8/2000 | Tihon et al. | |
| 6,117,067 A | 9/2000 | Gil-Vernet | |
| 6,127,597 A | 10/2000 | Beyar et al. | |
| 6,168,611 B1 | 1/2001 | Risvi | |
| 6,200,330 B1 | 3/2001 | Benderev et al. | |
| 6,221,005 B1 | 4/2001 | Bruckner et al. | |
| 6,241,736 B1 | 6/2001 | Sater et al. | |
| 6,245,082 B1 | 6/2001 | Gellman et al. | |
| 6,264,676 B1 | 7/2001 | Gellman et al. | |
| 6,273,852 B1 | 8/2001 | Lehe et al. | |
| 6,302,840 B1 | 10/2001 | Benderev | |
| 6,306,079 B1 | 10/2001 | Trabucco | |
| 6,322,492 B1 | 11/2001 | Kovac | |
| 6,328,686 B1 | 12/2001 | Kovac | |
| 6,328,744 B1 | 12/2001 | Harari et al. | |
| 6,334,446 B1 | 1/2002 | Beyar | |
| 6,382,214 B1 | 5/2002 | Raz et al. | |
| 6,387,041 B1 | 5/2002 | Harari et al. | |
| 6,406,423 B1 | 6/2002 | Scetbon | |
| 6,406,480 B1 | 6/2002 | Beyar et al. | |
| 6,423,080 B1 | 7/2002 | Gellman et al. | |
| 6,447,505 B2 * | 9/2002 | McGovern et al. | 606/41 |
| 6,451,024 B1 | 9/2002 | Thompson et al. | |
| 6,475,139 B1 | 11/2002 | Miller | |

(56) References Cited

U.S. PATENT DOCUMENTS

| | | |
|---|---|---|
| 6,478,727 B2 | 11/2002 | Scetbon |
| 6,482,214 B1 | 11/2002 | Sidor, Jr. et al. |
| 6,491,703 B1 | 12/2002 | Ulmsten |
| 6,502,578 B2 | 1/2003 | Raz et al. |
| 6,506,190 B1 | 1/2003 | Walshe |
| 6,530,943 B1 | 3/2003 | Hoepffner et al. |
| 6,544,273 B1 | 4/2003 | Harari et al. |
| 6,575,897 B1 | 6/2003 | Ory |
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin et al. |
| 6,635,058 B2 | 10/2003 | Beyar et al. |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman et al. |
| 6,691,711 B2 | 2/2004 | Raz |
| 6,699,175 B2 | 3/2004 | Miller |
| 6,702,827 B1 | 3/2004 | Lund |
| 6,730,110 B1 | 5/2004 | Harari et al. |
| 6,746,455 B2 | 6/2004 | Beyar et al. |
| 6,752,814 B2 | 6/2004 | Gellman et al. |
| 6,755,781 B2 | 6/2004 | Gellman |
| 6,802,807 B2 | 10/2004 | Anderson |
| 6,830,052 B2 | 12/2004 | Carter et al. |
| 6,881,184 B2 | 4/2005 | Zappala |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,953,428 B2 | 10/2005 | Gellman et al. |
| 6,960,160 B2 | 11/2005 | Browning |
| 6,969,347 B2 | 11/2005 | Miller |
| 6,971,986 B2 | 12/2005 | Staskin et al. |
| 6,974,462 B2 | 12/2005 | Sater |
| 6,979,317 B2 * | 12/2005 | Galt et al. ............ 604/158 |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,059 B2 | 8/2006 | Harari et al. |
| 7,087,065 B2 | 8/2006 | Ulmsten et al. |
| 7,112,171 B2 | 9/2006 | Rocheleau et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jaquetin |
| 7,175,591 B2 | 2/2007 | Kaladelfos |
| 7,198,597 B2 | 4/2007 | Siegel et al. |
| 7,223,229 B2 | 5/2007 | Inman et al. |
| 7,226,407 B2 | 6/2007 | Kammerer |
| 7,226,408 B2 | 6/2007 | Harai et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,267,645 B2 | 9/2007 | Anderson et al. |
| 7,273,448 B2 | 9/2007 | Siegel et al. |
| 7,291,104 B2 | 11/2007 | Neisz et al. |
| 7,297,102 B2 | 11/2007 | Smith et al. |
| 7,299,803 B2 | 11/2007 | Kovac |
| 7,303,525 B2 | 12/2007 | Watschke et al. |
| 7,326,213 B2 | 2/2008 | Benderev et al. |
| 7,347,812 B2 | 3/2008 | Mellier |
| 7,351,196 B2 | 4/2008 | Goldmann et al. |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,402,133 B2 | 7/2008 | Chu et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,431,690 B2 | 10/2008 | Merade et al. |
| 7,494,495 B2 | 2/2009 | Delorme et al. |
| 7,500,945 B2 | 3/2009 | Cox |
| 7,513,865 B2 | 4/2009 | Bourne et al. |
| 7,517,313 B2 | 4/2009 | Thierfelder et al. |
| 7,527,588 B2 | 5/2009 | Zaddem et al. |
| 7,527,633 B2 | 5/2009 | Rioux |
| 7,547,316 B2 | 6/2009 | Kammerer et al. |
| 7,588,598 B2 | 9/2009 | Delorme et al. |
| 7,601,118 B2 | 10/2009 | Smith et al. |
| 7,608,036 B2 | 10/2009 | Raz et al. |
| 7,611,454 B2 | 11/2009 | De Leval |
| 7,614,999 B2 | 11/2009 | Gellman et al. |
| 7,621,864 B2 | 11/2009 | Suslian et al. |
| 7,621,865 B2 | 11/2009 | Gellman et al. |
| 7,637,860 B2 | 12/2009 | MacLean |
| 7,686,759 B2 | 3/2010 | Sater |
| 7,686,760 B2 | 3/2010 | Anderson et al. |
| 7,691,050 B2 | 4/2010 | Gellman et al. |
| 7,691,052 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,762,969 B2 | 7/2010 | Gellman et al. |
| 7,766,926 B2 | 8/2010 | Bosley et al. |
| 7,789,821 B2 | 9/2010 | Browning |
| 7,794,385 B2 | 9/2010 | Rosenblatt |
| 2001/0018549 A1 | 8/2001 | Scetbon |
| 2001/0023356 A1 | 9/2001 | Raz |
| 2001/0041895 A1 | 11/2001 | Beyer et al. |
| 2001/0049467 A1 | 12/2001 | Lehe et al. |
| 2001/0053916 A1 | 12/2001 | Rioux |
| 2002/0007222 A1 | 1/2002 | Desai |
| 2002/0028980 A1 | 3/2002 | Thierfelder et al. |
| 2002/0055748 A1 | 5/2002 | Gellman et al. |
| 2002/0058959 A1 | 5/2002 | Gellman et al. |
| 2002/0068948 A1 | 6/2002 | Stormby et al. |
| 2002/0077526 A1 | 6/2002 | Kammerer et al. |
| 2002/0082619 A1 | 6/2002 | Cabak et al. |
| 2002/0091373 A1 | 7/2002 | Berger |
| 2002/0095163 A1 | 7/2002 | Beyer et al. |
| 2002/0099260 A1 | 7/2002 | Suslian et al. |
| 2002/0103542 A1 | 8/2002 | Bilbo |
| 2002/0107525 A1 | 8/2002 | Harari et al. |
| 2002/0115906 A1 | 8/2002 | Miller |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151909 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz |
| 2002/0188169 A1 | 12/2002 | Kammerer et al. |

(56) References Cited

U.S. PATENT DOCUMENTS

| | | |
|---|---|---|
| 2003/0004395 A1 | 1/2003 | Therin |
| 2003/0004581 A1 | 1/2003 | Rousseau |
| 2003/0009181 A1 | 1/2003 | Gellman et al. |
| 2003/0023136 A1 | 1/2003 | Raz |
| 2003/0023137 A1 | 1/2003 | Gellman et al. |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0073235 A1 | 4/2004 | Lund |
| 2004/0193215 A1 | 9/2004 | Harari et al. |
| 2004/0225181 A1* | 11/2004 | Chu et al. .................. 600/37 |
| 2004/0267088 A1 | 12/2004 | Kammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0038451 A1 | 2/2005 | Rao et al. |
| 2005/0055104 A1 | 3/2005 | Arnal et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0058578 A1 | 3/2006 | Browning |
| 2006/0089524 A1 | 4/2006 | Chu |
| 2006/0089525 A1* | 4/2006 | Mamo et al. .................. 600/37 |
| 2006/0122457 A1 | 6/2006 | Kovac |
| 2006/0173237 A1 | 8/2006 | Jacquetin |
| 2006/0195007 A1 | 8/2006 | Anderson |
| 2006/0195011 A1 | 8/2006 | Arnal |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0287571 A1 | 12/2006 | Gozzi |
| 2007/0015953 A1 | 1/2007 | MacLean |
| 2007/0078295 A1 | 4/2007 | Landgrebe |
| 2007/0173864 A1 | 7/2007 | Chu |
| 2008/0039678 A1 | 2/2008 | Montpetit et al. |
| 2008/0300607 A1 | 12/2008 | Meade et al. |
| 2009/0005634 A1 | 1/2009 | Rane |
| 2009/0012353 A1 | 1/2009 | Beyer |
| 2009/0221867 A1 | 9/2009 | Ogdahl et al. |
| 2009/0221868 A1 | 9/2009 | Evans |
| 2009/0259092 A1 | 10/2009 | Ogdahl et al. |
| 2010/0094079 A1 | 4/2010 | Inman |
| 2010/0168505 A1 | 7/2010 | Inman et al. |
| 2010/0261950 A1 | 10/2010 | Lund et al. |

FOREIGN PATENT DOCUMENTS

| | | |
|---|---|---|
| DE | 2305815 | 2/1973 |
| DE | 4220283 C2 | 5/1994 |
| DE | 19544162 | 4/1997 |
| DE | 10211360 | 9/2003 |
| DE | 20016866 | 3/2007 |
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 0941712 A1 | 9/1999 |
| EP | 1093758 A1 | 4/2001 |
| EP | 1060714 A3 | 9/2002 |
| EP | 1342450 B1 | 9/2003 |
| EP | 1320336 B1 | 7/2005 |
| FR | 2787990 A1 | 7/2000 |
| FR | 2852813 A1 | 1/2004 |
| GB | 2268690 A | 1/1994 |
| GB | 2353220 A | 10/2000 |
| IT | 1299162 | 4/1998 |
| SU | 1225547 A1 | 4/1986 |
| SU | 1342486 A | 10/1987 |
| WO | WO9310715 A1 | 6/1993 |
| WO | WO9317635 A1 | 9/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937217 A1 | 7/1999 |
| WO | WO9952450 A1 | 10/1999 |
| WO | WO9953844 A1 | 10/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0040158 A2 | 7/2000 |
| WO | WO0057812 A1 | 10/2000 |
| WO | WO0066030 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |
| WO | WO0139670 A1 | 6/2001 |
| WO | WO0145588 A1 | 6/2001 |
| WO | WO0145589 A1 | 6/2001 |
| WO | WO0156499 A1 | 8/2001 |
| WO | WO0222184 A2 | 3/2002 |
| WO | WO0228312 A1 | 4/2002 |
| WO | WO0228315 A2 | 4/2002 |
| WO | WO0230293 A1 | 4/2002 |
| WO | WO0232284 A2 | 4/2002 |
| WO | WO0234124 A2 | 5/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02078552 A1 | 10/2002 |
| WO | WO02088704 A2 | 11/2002 |
| WO | WO02091950 A1 | 11/2002 |
| WO | WO03013392 A2 | 2/2003 |
| WO | WO03017848 A1 | 3/2003 |
| WO | WO03003778 A1 | 4/2003 |
| WO | WO03028585 A2 | 4/2003 |
| WO | WO03034939 A1 | 5/2003 |
| WO | WO03037215 A2 | 5/2003 |
| WO | WO03041613 A1 | 5/2003 |
| WO | WO03047435 A2 | 6/2003 |
| WO | WO03047476 A1 | 6/2003 |
| WO | WO03068107 A1 | 8/2003 |
| WO | WO03073960 A1 | 9/2003 |
| WO | WO03075792 A1 | 9/2003 |
| WO | WO03086205 A2 | 10/2003 |
| WO | WO03092546 A2 | 11/2003 |
| WO | WO03096928 A1 | 11/2003 |
| WO | WO03096929 A1 | 11/2003 |
| WO | WO2004012626 A1 | 2/2004 |
| WO | WO2004016196 A2 | 2/2004 |
| WO | WO2004017862 A2 | 3/2004 |
| WO | WO2004034912 A1 | 4/2004 |
| WO | WO2004041115 A1 | 5/2004 |
| WO | WO2004045457 A1 | 6/2004 |
| WO | WO2005004727 A1 | 1/2005 |
| WO | WO2005037132 A2 | 4/2005 |
| WO | WO2005046511 A2 | 5/2005 |

(56) References Cited

FOREIGN PATENT DOCUMENTS

| | | |
|---|---|---|
| WO | WO2005048850 A2 | 6/2005 |
| WO | WO2005079702 A1 | 9/2005 |
| WO | WO2005087153 A2 | 9/2005 |
| WO | WO2005094741 A1 | 10/2005 |
| WO | WO2005112842 A1 | 12/2005 |
| WO | WO2005122954 A1 | 12/2005 |
| WO | WO2006007189 A1 | 1/2006 |
| WO | WO2006007190 A1 | 1/2006 |
| WO | WO2006015031 A2 | 2/2006 |
| WO | WO2006031879 A1 | 3/2006 |
| WO | WO2006108145 A1 | 10/2006 |
| WO | WO2007002012 A1 | 1/2007 |
| WO | WO2007002071 A1 | 1/2007 |
| WO | WO2007011341 A1 | 1/2007 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994 | 8/2007 |
| WO | WO2007137226 A2 | 11/2007 |
| WO | WO2007137226 A3 | 11/2007 |
| WO | WO2007146784 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |

OTHER PUBLICATIONS

"Introducing: AlloSling Fascia The Natural Choice for Suburethral Sling Procedures", Advertisement from UroMed Corporation (1 page).

"We're staying ahead of the curve" Introducing the IVS Tunneller Device for Tension Free Procedures, Tyco Healthcare, 3 pages (2002).

Advantage A/T™, Surgical Mesh Sling Kit, Boston Scientific, 6 pages (2002).

Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).

AlloSource product literature (11pages).

Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).

Araki, Tohru et al., The Loop-Loosening Procedure for Urination Difficulties After Stamey Suspension of the Vesical Neck, The Journal of Urology, vol. 144, pp. 319-323 (Aug. 1990).

Asmussen, M. et.al., Simultaneous Urethro-Cystometry With a New Technique, Scand J Urol Nephrol 10, p. 7-11 (1976).

Beck, Peter R. et al., Treatment of Urinary Stress Incontinence With Anterior Colporrhaphy, Obstetrics and Gynecology, vol. 59 (No. 3), pp. 269-274 (Mar. 1982).

Benderev, Theodore V., MD, A Modified Percutaneous Outpatient Bladder Neck Suspension System, Journal of Urology, vol. 152, pp. 2316-2320 (Dec. 1994).

Benderev, Theodore V., MD, Anchor Fixation and Other Modifications of Endoscopic Bladder Neck Suspension, Urology, vol. 40, No. 5, pp. 409-418 (Nov. 1992).

Bergman, Arieh et al., Three Surgical Procedures for Genuine Stress Incontinence: Five-Year Follow-Up of a Prospective Randomized Study, Am J Obstet Gynecol, vol. 173 No. 1, pp. 66-71 (Jul. 1995).

Blaivas, Jerry et al., Pubovaginal Fascial Sling for the Treatment of Complicated Stress Urinary Incontinence, The Journal of Urology, vol. 145, pp. 1214-1218 (Jun. 1991).

Blaivas, Jerry et al., Type III Stress Urinary Incontinence: Importance of Proper Diagnosis and Treatment, Surgical Forum, pp. 473-475, (1984).

Blaivas, Jerry, Commentary: Pubovaginal Sling Procedure, Experience with Pubovaginal Slings, pp. 93-101 (1990).

Boyles, Sarah Hamilton et al., Procedures for Urinary Incontinence in the United States, 1979-1997, Am J Obstet Gynecol, vol. 189, n. 1, pp. 70-75 (Jul. 2003).

Bryans, Fred E., Marlex Gauze Hammock Sling Operation With Cooper's Ligament Attachment in the Management of Recurrent Urinary Stress Incontinence, American Journal of Obstetrics and Gynecology, vol. 133, pp. 292-294 (Feb. 1979).

Burch, John C., Urethrovaginal Fixation to Cooper's Ligament for Correction of Stress Incontinence, Cystocele, and Prolapse, Am. J. Obst. & Gyn, vol. 31, pp. 281-290 (1961).

Capio™ CL—Transvaginal Suture Capturing Device—Transvaginal Suture Fixation to Cooper's Ligament for Sling Procedures, Boston Scientific, Microvasive®, 8 pages, (2002).

Cervigni, Mauro et al., The Use of Synthetics in the Treatment of Pelvic Organ Prolapse, Voiding Dysfunction and Female Urology, vol. 11, pp. 429-435 (2001).

Choe, Jong M. et al., Gore-Tex Patch Sling: 7 Years Later, Urology, vol. 54, pp. 641-646 (1999).

Comparison of Tissue Reaction of Monofilament and Multifilament Polypropylene Mesh—A Case Report, Tyco Healthcare, United States Surgical, 4 pages (no date).

Cook/Ob Gyn®, Urogynecology, Copyright Cook Urological Inc., pp. 1-36 (1996).

Dargent, D. et al., Insertion of a Suburethral Sling Through the Obturator Membrane in the Treatment of Female Urinary Incontinence, Gynecol Obstet Fertil, vol. 30, pp. 576-582 (2002).

Das, Sakti et al., Laparoscopic Colpo-Suspension, The Journal of Urology, vol. 154, pp. 1119-1121 (Sep. 1995).

Debodinance, Philipp et al., "Tolerance of Synthetic Tissues in Touch With Vaginal Scars: Review to the Point of 287 Cases", Europeon Journal of Obstetrics & Gynecology and Reproductive Biology 87 (1999) pp. 23-30.

Decter, Ross M., Use of the Fascial Sling for Neurogenic Incontinence: Lessons Learned, The Journal of Urology, vol. 150, pp. 683-686 (Aug. 1993).

Delancey, John, MD, Structural Support of the Urethra as It Relates to Stress Urinary Incontinence: The Hammock Hypothesis, Am J Obstet Gynecol, vol. 170 No. 6, pp. 1713-1723 (Jun. 1994).

Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.

Diana, et al., Treatment of Vaginal Vault Prolapse With Abdominal Sacral Colpopexy Using Prolene Mesh, American Journal of Surgery, vol. 179, pp. 126-128, (Feb. 2000).

Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).

Enzelsberger, H. et al., Urodynamic and Radiologic Parameters Before and After Loop Surgery for Recurrent Urinary Stress Incontinence, Acta Obstet Gynecol Scand, 69, pp. 51-54 (1990).

Eriksen, Bjarne C. et al., Long-Term Effectiveness of the Burch Colposuspension in Female Urinary Stress Incontinence, Acta Obstet Gynecol Scand, 69, pp. 45-50 (1990).

Falconer, C. et al., Clinical Outcome and Changes in Connective Tissue Metabolism After Intravaginal Slingplasty in Stress Incontinence Women, International Urogynecology Journal, pp. 133-137 (1966).

Falconer, C. et al., Influence of Different Sling Materials of Connective Tissue Metabolism in Stress Urinary Incontinent Women, International Urogynecology Journal, Supp. 2, pp. S19-S23 (2001).

Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).

Farquhar, Cynthia M. et al., Hysterectomy Rates in the United States 1990-1997, Obstetrics & Gynecology, vol. 99, n. 2, pp. 229-234 (Feb. 2002).

Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6 (Dec. 1996).

(56) References Cited

OTHER PUBLICATIONS

Flood, C.G. et al., Anterior Colporrhaphy Reinforce With Marlex Mesh for the Treatment of Cystoceles, International Urogynecology Journal, vol. 9, pp. 200-204 (1998).
Gilja, Ivan et al., A Modified Raz Bladder Neck Suspension Operation (Transvaginal Burch), The Journal of Urology, vol. 153, pp. 1455-1457 (May 1995).
Gittes, Ruben F. et al., No-Incision Pubovaginal Suspension for Stress Incontinence, The Journal of Urology, vol. 138 (Sep. 1987).
Guner, et al., Transvaginal Sacrospinous Colpopexy for Marked Uterovaginal and Vault Prolapse, Inter J of Gynec & Obstetrics, vol. 74, pp. 165-170 (2001).
Gynecare TVT Tension-Free Support for Incontinence, The tension-free solution to female Incontinence, Gynecare Worldwide,6 pages, (2002).
Handa, Victoria L. et al, Banked Human Fascia Lata for the Suburethral Sling Procedure: A Preliminary Report, Obstetrics & Gynecology, vol. 88 No. 6, 5 pages (Dec. 1996).
Heit, Michael et al., Predicting Treatment Choice for Patients With Pelvic Organ Prolapse, Obstetrics & Gynecology, vol. 101, n. 6, pp. 1279-1284 (Jun. 2003).
Henriksson, L. et al., A Urodynamic Evaluation of the Effects of Abdominal Urethrocystopexy and Vaginal Sling Urethroplasty in Women With Stress Incontinence, Am. J. Obstet. Gynecol. vol. 131, No. 1, pp. 77-82 (Mar. 1, 1978).
Hodgkinson, C. Paul et.al., Urinary Stress Incontinence in the Female, Department of Gynecology and Obstetrics, Henry Ford Hospital, vol. 10, No. 5, p. 493-499, (Nov. 1957).
Holschneider, C. H., et al., The Modified Pereyra Procedure in Recurrent Stress Urinary Incontinence: A 15-year Review, Obstetrics & Gynecology, vol. 83, No. 4, pp. 573-578 (Apr. 1994).
Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648-652 (Apr. 1998).
Ingelman-Sunberg, A. et al., Surgical Treatment of Female Urinary Stress Incontinence, Contr. Gynec. Obstet., vol. 10, pp. 51-69 (1983).
Intramesh L.I.F.T. Siliconized polyester, Cousin Biotech, 1 page (no date).
Intramesh® L.I.F.T.® Polypropylene Less Invasive Free Tape, Cousin Biotech, 2 pages (no date).
IVS Tunneller—A Universal instrument for anterior and posterior intra-vaginal tape placement, Tyco Healthcare, 4 pages (Aug. 2002).
IVS Tunneller—ein universelles Instrument fur die Intra Vaginal Schlingenplastik, Tyco Healthcare, 4 pages (2001).
IVS Tunneller, AMA, (no. date) 4 pages.
IVS Tunneller, Australian Medical Design Breakthrough for GSI, mixed incontinence and vault prolapse, AMA Medical Products, 4 pages (no date).
Jeffcoate, T.N.A. et al., The Results of the Aldridge Sling Operation for Stress Incontinence, Journal of Obstetrics and Gynaecology, pp. 36-39 (1956).
Jones, N.H.J. Reay et al., Pelvic Connective Tissue Resilience Decreases With Vaginal Delivery, Menopause and Uterine Prolapse, Br J Surg, vol. 90, n. 4, pp. 466-472 (Apr. 2003).
Julian, Thomas, The Efficacy Prolapse of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).
Karram, Mickey et al., Patch Procedure: Modified Transvaginal Fascia Lata Sling for Recurrent for Severe Stress Urinary Incontinence, vol. 75, pp. 461-463 (Mar. 1990).
Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).
Kersey, J., The Gauze Hammock Sling Operation in the Treatment of Stress Incontinence, British Journal of Obstetrics and Gynaecology, vol. 90, pp. 945-949 (Oct. 1983).

Klutke, Carl et al., The Anatomy of Stress Incontinence: Magentic Resonance Imaging of the Female Bladder Neck and Urethra, The Journal of Urology, vol. 143, pp. 563-566 (Mar. 1990).
Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).
Klutke, John M.D. et al, The promise of tension-free vaginal tape for female SUI, Contemporary Urology, 7 pages (Oct. 2000).
Korda, A. et al., Experience With Silastic Slings for Female Urinary Incontience, Aust NZ J. Obstet Gynaecol, vol. 29, pp. 150-154 (May 1989).
Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).
Kovac, S. Robert, et al, Pubic Bone Suburethral Stabilization Sling: A Long Term Cure for SUI?, Contemporary OB/GYN, 10 pages (Feb. 1998).
Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).
Kovac, Stephen Robert, M.D., Cirriculum Vitae, pp. 1-33 (Jun. 18, 1999).
Leach, Gary E., et al., Female Stress Urinary Incontinence Clinical Guidelines Panel Report on Surgical Management of Female Stress Urinary Incontinence, American Urological Association, vol. 158, pp. 875-880 (Sep. 1997).
Leach, Gary E., MD, Bone Fixation Technique for Transvaginal Needle Suspension, Urology vol. XXXI, No. 5, pp. 388-390 (May 1988).
Lichtenstein, Irving L. et al, The Tension Free Hernioplasty, The American Journal of Surgery, vol. 157 pp. 188-193 (Feb. 1989).
LigiSure Atlas™, Tyco Healthcare, Valleylab®, 2 pages (no date).
Loughlin, Kevin R. et al., Review of an 8-Year Experience With Modifications of Endoscopic Suspension of the Bladder Neck for Female Stress Incontinence, The Journal of Uroloyg, vol. 143, pp. 44-45 (1990).
Luber, Karl M. et al., The Demographics of Pelvic Floor Disorders; Current Observations and Future Projections, Am J Obstet Gynecol, vol. 184, n. 7, pp. 1496-1503 (Jun. 2001).
Mage, Technique Chirurgicale, L'Interpostion D'Un Treillis Synthetique Dans La Cure Par Voie Vaginale Des Prolapsus Genitaux, J Gynecol Obstet Biol Reprod, vol. 28, pp. 825-829 (1999).
Marchionni, Mauro et al., True Incidence of Vaginal Vault Prolapse—Thirteen Years of Experience, Journal of Reproductive Medicine, vol. 44, n. 8, pp. 679-684 (Aug. 199).
Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).
Marshall, Victor Fray et al. The Correction of Stress Incontinence by Simple Vesicourethral Suspension, Surgery, Gynecology and Obstetrics, vol. 88, pp. 509-518 (1949).
McGuire, Edward J. et al., Pubovaginal Sling Procedure for Stress Incontinence, The Journal of Urology, vol. 119, pp. 82-84 (Jan. 1978).
McGuire, Edward J. et al., Abdominal Procedures for Stress Incontinence, Urologic Clinics of North America, pp. 285-290, vol. 12, No. 2 (May 1985).
McGuire, Edward J. et al., Experience With Pubovaginal Slings for Urinary Incontinence at the University of Michigan, Journal of Urology, vol. 138, pp. 90-93(1987).
McGuire, Edward J. et al., Abdominal Fascial Slings, Slings, Raz Female Urology, p. 369-375 (1996).
McGuire, Edwared J., M.D., The Sling Procedure for Urinary Stress Incontinence, Profiles in Urology, pp. 3-18.
McGuire™ Suture Buide, The McGuire™ Suture Guide, a single use instrument designed for the placement of a suburethral sling, Bard, 2 pages (2001).
McIndoe, G. A. et al., The Aldridge Sling Procedure in the Treatment of Urinary Stress Incontinence, Aust. N Z Journal of Obstet Gynecology, pp. 238-239 (Aug. 1987).
McKiel, Charles F. Jr., et al, Marshall-Marchetti Procedure Modification, vol. 96, pp. 737-739 (Nov. 1966).

(56) References Cited

OTHER PUBLICATIONS

Migliari, Roberto et al., Tension-Free Vaginal Mesh Repair for Anterior Vaginal Wall Prolapse, Eur Urol, vol. 38, pp. 151-155 (Oct. 1999).
Migliari, Roberto et al., Treatment Results Using a Mixed Fiber Mesh in Patients With Grade IV Cystocele, Journal of Urology, vol. 161, pp. 1255-1258 (Apr. 1999).
Mitek Brochure, Therapy of Urinary Stess Incontinence in Women Using Mitek GIII Anchors, by Valenzio C. Mascio, MD.
Moir, J. Chassar et.al., The Gauze-Hammock Operation, The Journal of Obstetrics and Gynaecology of British Commonwealth, vol. 75 No. 1, pp. 1-9 (Jan. 1968).
Morgan, J. E., A Sling Operation, Using Marlex Polypropylene Mesh, for the Treatment of Recurrent Stress Incontinence, Am. J. Obst. & Gynecol, pp. 369-377 (Feb. 1970).
Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).
Morley, George W. et al., Sacrospinous Ligament Fixations for Eversion of the Vagina, Am J Obstet Gyn, vol. 158, n. 4, pp. 872-881 (Apr. 1988).
Narik, G. et.al., A Simplified Sling Operation Suitable for Routine Use, Gynecological and Obstetrical Clinic, University of Vienna, vol. 84, No. 3, p. 400-405, (Aug. 1, 1962).
Natale, F. et al., Tension Free Cystocele Repair (TCR): Long-Term Follow-Up, International Urogynecology Journal, vol. 11, supp. 1, p. S51 (Oct. 2000).
Nichols, David H., The Mersilene Mesh Gauze-Hammock for Severe Urinary Stress Incontinence, Obstetrics and Gynecology, vol. 41, pp. 88-93 (Jan. 1973).
Nicita, Giulio, A New Operation for Genitourinary Prolapse, Journal of Urology, vol. 160, pp. 741-745 (Sep. 1998).
Niknejad, Kathleen et al., Autologous and Synthetic Urethral Slings for Female Incontinence, Urol Clin N Am, vol. 29, pp. 597-611 (2002).
Norris, Jeffrey P. et al., Use of Synthetic Material in Sling Surgery: A Minimally Invasive Approach, Journal of Endourology, vol. 10, pp, 227-230 (Jun. 1996).
O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).
Ostergard, Donald R. et al., Urogynecology and Urodynamics Theory and Practice, pp. 569-579 (1996).
Paraiso et al., Laparoscopic Surgery for Enterocele, Vaginal Apex Prolapse and Rectocele, Int. Urogynecol J, vol. 10, pp. 223-229 (1999).
Parra, R. O., et al, Experience With a Simplified Technique for the Treatment of Female Stress Urinary Incontinence, British Journal of Urology, pp. 615-617 (1990).
Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45-50 (1999).
Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).
Pereyra, Armand J., M.D., F.A.C.S., A Simplified Surgical Procedure for Correction of Stress Incontinence in Women, West.J.Surg., Obst. & Gynec, p. 223-226, (Jul.-Aug. 1959).
Peter E. Papa Petros et al., Cure of Stress Incontinence by Repair of External Anal Sphincter, Acta Obstet Gynecol Scand, vol. 69, Sup 153, p. 75 (1990).
Peter Petros et al., Anchoring the Midurethra Restores Bladder-Neck Anatomy and Continence, The Lancet, vol. 354, pp. 997-998 (Sep. 18, 1999).
Petros, Peter E. Papa et al., An Anatomical Basis for Success and Failure of Female Incontinence Surgery, Scandinavian Journal of Neurourology and Urodynamics, Sup 153, pp. 55-60 (1993).

Petros, Peter E. Papa et al., An Analysis of Rapid Pad Testing and the History for the Diagnosis of Stress Incontinence, Acta Obstet Gynecol Scand, vol. 71, pp. 529-536 (1992).
Petros, Peter E. Papa et al., An Integral Theory of Female Urinary Incontinence, Acta Obstetricia et Gynecologica Scandinavica, vol. 69 Sup. 153, pp. 7-31 (1990).
Petros, Peter E. Papa et al., Bladder Instability in Women: A Premature Activation of the Micturition Reflex, Scandinavian Journal of Neurourology and Urodynamics, Sup 153, pp. 235-239 (1993).
Petros, Peter E. Papa et al., Cough Transmission Ratio: An Indicator of Suburethral Vaginal Wall Tension Rather Than Urethral Closure, Acta Obstet Gynecol Scand, vol. 69, Sup 153, pp. 37-39 (1990).
Petros, Peter E. Papa et al., Cure of Urge Incontinence by the Combined Intravaginal Sling and Tuck Operation, Acta Obstet Gynecol Scand, vol. 69, Sup 153, pp. 61-62 (1990).
Petros, Peter E. Papa et al., Further Development of the Intravaginal Slingplasty Procedure—IVS III—(With Midline "Tuck"), Scandinavian Journal of Neurourology and Urodynamics. Sup 153, p. 69-71 (1993).
Petros, Peter E. Papa et al., Medium-Term Follow-Up of the Intravaginal Slingplasty Operaton Indicates Minimal Deterioration of Urinary Continence With Time, (3 pages) (1999).
Petros, Peter E. Papa et al., Non Stress Non Urge Female Urinary Incontinence—Diagnosis and Cure: A Preliminary Report, Acta Obstet Gynecol Scand, vol. 69, Sup 153, pp. 69-70 (1990).
Petros, Peter E. Papa et al., Part I: Theoretical, Morphological, Radiographical Correlations and Clinical Perspective, Scandinavian Journal of Neurourology and Urodynamics, Sup 153, pp. 5-28 (1993).
Petros, Peter E. Papa et al., Part II: The Biomechanics of Vaginal Tissue and Supporting Ligaments With Special Relevance to the Pathogenesis of Female Urinary Incontinence, Scandinavian Journal of Neurourology and Urodynamics, Sup 153, pp. 29-40 plus cover sheet (1993).
Petros, Peter E. Papa et al., Part III: Surgical Principles Deriving From the Theory, Scandinavian Journal of Neurourology and Urodynamics, Sup 153, pp. 41-52 (1993).
Petros, Peter E. Papa et al., Part IV: Surgical Appliations of the Theory—Development of the Intravaginal Sling Pklasty (IVS) Procedure, Scandinavian Journal of Neurourology and Urodynamics. Sup 153, pp. 53-54 (1993).
Petros, Peter E. Papa et al., Pelvic Floor Rehabilitation According to the Integrated Theory of Female Urinary Incontinence, Chapter 7, pp. 249-258 (book chapter).
Petros, Peter E. Papa et al., Pinch Test for Diagnosis of Stress Urinary Incontinence, Acta Obstet Gynecol Scand, vol. 69, Sup 153, pp. 33-35 (1990).
Petros, Peter E. Papa et al., Pregnancy Effects on the Intravaginal Sling Operation, Acta Obstet Gynecol Scand, vol. 69, Sup 153, pp. 77-79 (1990).
Petros, Peter E. Papa et al., The Autogenic Ligament Procedure: A Technique for Planned Formation of an Artificial Neo-Ligament, Acta Obstet Gynecol Scand, vol. 69, Sup 153, pp. 43-51 (1990).
Petros, Peter E. Papa et al., The Combined Intravaginal Sling and Tuck Operation an Ambulatory Procedure for Cure of Stress and Urge Incontinence, Acta Obstet Gynecol Scand, vol. 69, Sup 153, pp. 53-59 (1990).
Petros, Peter E. Papa et al., The Development of the Intravaginal Slingplasty Procedure: IVS II—(With Bilateral "Tucks"), Scandinavian Journal of Neurourology and Urodynamics, Sup 153, pp. 61-67 (1993).
Petros, Peter E. Papa et al., The Free Graft Procedure for Cure of the Tethered Vagina Syndrome, Scandinavian Journal of Neurourology and Urodynamics, Sup 153, pp. 85-87(1993).
Petros, Peter E. Papa et al., The Further Development of the Intravaginal Slingplasty Procedure—IVS IV—(With "Double Breasted" Unattached Vaginal Flap Repair and "Free" Vaginal Tapes), Scandinavian Journal of Neurourology and Urodynamics, Sup 153, p. 73-75 (1993).
Petros, Peter E. Papa et al., The Futher Development of the Intravaginal Slingplasty Procedure—IVS V—(With "Double

(56) References Cited

OTHER PUBLICATIONS

Breasted" Unattached Vaginal Flap Repair and Permanent Sling)., Scandinavian Journal of Neurourology and Urodynamics, Sup 153, pp. 77-79 (1993).
Petros, Peter E. Papa et al., The Intravaginal Slingplasty Operation, A Minimally Invasive Technique for Cure of Urinary Incontinence in the Female, Aust. NZ J Obstet Gynaecol, vol. 36, n. 4, pp. 453-461 (1996).
Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81-84 (1993).
Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pp. 89-93 (1993).
Petros, Peter E. Papa et al., The Role of a Lax Posterior Vaginal Fornix in the Causation of Stress and Urgency Symptoms: A Preliminary Report, Acta Obstet Gynecol Scand, vol. 69, Sup 153, pp. 71-73 (1990).
Petros, Peter E. Papa et al., The Tethered Vagina Syndrome, Post Surgical Incontinence and I-Plasty Operation for Cure, Acta Obstet Gynecol Scand, vol. 69, Sup 153, pp. 63-67 (1990).
Petros, Peter E. Papa et al., The Tuck Procedure: A Simplified Vaginal Repair for Treatment of Female Urinary Incontinence, Acta Obstet Gynecol Scand, vol. 69, Sup 153, pp. 41-42 (1990).
Petros, Peter E. Papa et al., Urethral Pressure Increase on Effort Originates From Within the Urethra, and Continence From Musculovaginal Closure, Scandinavian Journal of Neurourology and Urodynamics, pp. 337-350 (1995).
Petros, Peter E. Papa, Development of Generic Models for Ambulatory Vaginal Surgery—Preliminary Report, International Urogynecology Journal, pp. 20-27 (1998).
Petros, Peter E. Papa, New Ambulatory Surgical Methods Using an Anatomical Classification of Urinary Dysfunction Improves Stress, Urge and Abnormal Emptying, Int. Urogynecology Journal Pelvic Floor Dysfunction, vol. 8 (5), pp. 270-278, (1997).
Petros, Peter E. Papa, Vault Prolapse II; Restoration of Dynamic Vaginal Supports by Infracoccygeal Sacropexy, an Axial Day-Case Vaginal Procedure, Int Urogynecol J. vol. 12, pp. 296-303 (2001).
Rackley, Raymond R. et al., Tension-Free Vaginal Tape and Percutaneous Vaginal Tape Sling Procedures, Techniques in Urology, vol. 7, No. 2, pp. 90-100 (2001).
Rackley, Raymond R. M.D., Synthetic Slings: Five Steps for Successful Placement, Urology Times, pp. 46,48,49 (Jun. 2000).
Raz, Shlomo, et al., The Raz Bladder Neck Suspension Results in 206 Patients, The Journal of Urology, pp. 845-846 (1992).
Raz, Shlomo, Female Urology, pp. 80-86, 369-398, 435-442 (1996).
Raz, Shlomo, MD, Modified Bladder Neck Suspension for Female Stress Incontinence, Urology, vol. XVII, No. 1, pp. 82-85 (Jan. 1981).
Readjustable REMEEX® system, Neomedic International, 8 pages (no date).
Richardson, David A. et al., Delayed Reaction to the Dacron Buttress Used in Urethropexy, The Journal of Reproductive Medicine, pp. 689-692, vol. 29, No. 9 (Sep. 1984).
Richter, K., Massive Eversion of the Vagina: Pathogenesis, Diagnosis and Therapy of the "True" Prolapse of the Vaginal Stump, Clin obstet gynecol, vol. 25, pp. 897-912 (1982).
Ridley, John H., Appraisal of The Goebell-Frangenheim-Stoeckel Sling Procedure, American Journal Obst & Gynec., vol. 95, No. 5, pp. 741-721 (Jul. 1, 1986).
Roberts, Henry, M.D., Cystourethrography in Women, Deptment of Obstetrics and Gynaecology, University of Liverpool, May 1952, vol. XXXV, No. 293, pp. 253-259.
SABRE™ Bioabsorbable Sling, Generation Now, Mentor, 4 pages (May 2002).
SABRE™ Surgical Procedure, Mentor, 6 pages (Aug. 2002).

Sanz, Luis E. et al., Modification of Abdominal Sacrocolpopexy Using a Suture Anchor System, The Journal of Reproductive Medicine, vol. 48, n. 7, pp. 496-500 (Jul. 2003).
Seim, Arnfinn et al., A Study of Female Urinary Incontinence in General Practice—Demography, Medical History, and Clinical Findings, Scand J Urol Nephrol, vol. 30, pp. 465-472 (1996).
Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).
Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).
Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).
Stamey, Thomas A., M.D., Endoscopic Suspension of the Vesical Neck for Urinary Incontinence in Females, Ann. Surgery, vol. 192 No. 4, pp. 465-471 (Oct. 1980).
Stanton, Stuart L., Suprapubic Approaches for Stress Incontinence in Women, Journal of American Geriatrics Society, vol. 38, No. 3, pp. 348-351 (Mar. 1990).
Stanton, Stuart, Springer-Veglag, Surgery of Female Incontinence, pp. 105-113 (1986).
Staskin et al., A Comparison of Tensile Strength among Three Preparations of Irradiated and Non-Irradiated Human Fascia Lata Allografts (2 pages).
Staskin, David R. et al., The Gore-Tex Sling Procedure for Female Sphincteric Incontinence: Indications, Technique, and Results, World Journal of Urology, vol. 15, pp. 295-299 (1997).
Studdiford, William E., Transplantation of Abdominal Fascia for the Relief of Urinary Stress Incontinence, American Journal of Obstetrics and Gynecology, pp. 764-775 (1944).
Subak, Leslee L. et al., Cost of Pelvic Organ Prolapse Surgery in the United States, Obstetrics & Gynecology, vol. 98, n. 4, pp. 646-651 (Oct. 2001).
Sullivan, Eugene S. et al., Total Pelvic Mesh Repair a Ten-Year Experience, Dis. Colon Rectum, vol. 44, No. 6, pp. 857-863 (Jun. 2001)
Suport™, Sub-Urethral Perineal Retro-Pubic Tensionless Sling, Matrix Medical (Pty) Ltd, (no date), 1 pg.
Swift, S.E., et al., Case-Control Study of Etiologic Factors in the Development of Sever Pelvic Organ Prolapse, Int Urogynecol J, vol. 12, pp. 187-192 (2001).
T-Sling® (Totally Tension-free) Urinary Incontinence Procedure, Herniamesh, 2 pages (no date).
TVT Tension-free Vaginal Tape, Gynecare, Ethicon, Inc., 23 pages (1999).
Ulmsten, U. et al., A Multicenter Study of Tension-Free Vaginal Tape (TVT) for Surgical Treatment of Stress Urinary Incontinence, International Urogynecology Journal, vol. 9, pp. 210-213 (1998).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, U., Female Urinary Incontinence—A Symptom, not a Urodynamic Disease. Some Theoretical and Pratical Aspects on the Diagnosis a Treatment of Female Urinary Incontinence, International Urogynecology Journal, vol. 6, pp. 2-3 (1995).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).
Ulmsten, Ulf et al., Different Biochemical Composition of Connective Tissue in Continent, Acta Obstet Gynecol Scand, pp. 455-457 (1987).
Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).
Ulmsten, Ulf et al., The Unstable Female Urethra, Am. J. Obstet. Gynecol., vol. 144 No. 1, pp. 93-97 (Sep. 1, 1982).

(56) References Cited

OTHER PUBLICATIONS

UroMed Access Instrument System for the Sub-urethral Sling Procedure Catalog No. 120235, Directions for Use, (3 pages).

Vesica® Percutaneous Bladder Neck Stabilization Kit, A New Approach to Bladder Neck Suspenison, Microvasive® Boston Scientific Corporation, 4 pages (1995).

Vesica® Sling Kits, Simplifying Sling Procedures, Microvasive® Boston Scientific Corporation, 4 pages (1998).

Villet, R., Réponse De R. Villet À L'Article De D. Dargent et al., Gynécolgie Obstétrique & Fertilité, vol. 31, p. 96 (2003).

Visco, Anthony G. et al., Vaginal Mesh Erosion After Abdominal Sacral Colpopexy, Am J Obstet Gynecol, vol. 184, n. 3, pp. 297-302 (297-302).

Walters, Mark D., Percutaneous Suburethral Slings: State of the Art, Presented at the conference of the American Urogynecologic Society, Chicago, 29 pages (Oct. 2001).

Waxman, Steve et al., Advanced Urologic Surgery for Urinary Incontinence, The Female Patient, pp. 93-100, vol. 21 (Mar. 1996).

Weber, Anne M. et al., Anterior Vaginal Prolapse: Review of Anatomy and Techniques of Surgical Repair, Obstetrics and Gynecology, vol. 89, n. 2, pp. 311-318 (Feb. 1997).

Webster, George D., Female Urinary Incontinence, Urologic Surgery, pp. 665-679.

Webster, George et al., Voiding Dysfunction Following Cystourethropexy: Its Evaluation and Management, The Journal of Urology, vol. 144, pp. 670-673 (Sep. 1990).

Winter, Chester C., Peripubic Urethropexy for Urinary Stress Incontinence in Women, Urology, vol. XX, No. 4, pp. 408-411 (Oct. 1982).

Winters et al., Abdominal Sacral Colpopexy and Abdominal Enterocele Repair in the Management of Vaginal Vault Prolapse, Urology, vol. 56, supp. 6A, pp. 55-63 (2000).

Woodside, Jeffrey R. et al., Suprapubic Endoscopic Vesical Neck Suspension for the Management of Urinary Incontinence in Myelodysplastic Girls, The Journal of Urology, vol. 135, pp. 97-99 (Jan. 1986).

Zacharin, Robert et al., Pulsion Enterocele: Long-Term Results of an Abdominoperineal Technique, Obstetrics & Gynecology, vol. 55 No. 2, pp. 141-148 (Feb. 1980).

Zacharin, Robert, The Suspensory Mechanism of the Female Urethra, Journal of Anatomy, vol. 97, Part 3, pp. 423-427 (1963).

Zimmern, Phillippe E. et al., Four-Corner Bladder Neck Suspension, Vaginal Surgery for the Urologist, vol. 2, No. 1, pp. 29-36 (Apr. 1994).

Le point sur l'incontinence urinaire, Expertise et Practiques en Urologie, No. 3. Dr. Sophie Conquy [Hospital Cochin, Paris]. pp. 17-19.

Mouly, Patrick et al., Vaginal Reconstruction of a Complete Vaginal Prolapse: The Trans Obturator Repair, Journal of Urology, vol. 169, p. 183 (Apr. 2003).

Pourdeyhimi, B, Porosity of Surgical Mesh Fabrics: New Technology, J. Biomed. Mater. Res.: Applied Biomaterials, vol. 23, No. A1, pp. 145-152 (1989).

Drutz, H.P. et al., Clinical and Urodynamic Re-Evaluation of Combined Abdominovaginal Marlex Sling Operations for Recurrent Stress Urinary Incontinence, International Urogynecology Journal, vol. 1, pp. 70-73 (1990).

Petros, Papa PE et al., An Integral Theory and Its Method for the Diagnosis and Management of Female Urinary Incontinence, Scandinavian Journal of Urology and Nephrology, Supplement 153: p. 1 (1993).

Horbach, Nicollette, Suburethral Sling Procedures, Genuine Stress Incontinence, Chapter 42, pp. 569-579.

Mentor Porges, Uratape, ICS/IUGA Symp, Jul. 2002.

Kettel, L. Michael et al., An Anatomical Evaluation of the Sacrospinous Ligament Colpopexy, Surg. Gynecol. Obstet., 168(4):318-22, Apr. 1989.

Flynn, B.J. et al., Surgical Management of the Apical Vaginal Defect, Curr. Opin. Urol. 12(4):353-58, Jul. 2002.

Buller, J.L. et al., Uterosacral Ligament: Description of Anatomic Relationships to Optimize Sergical Safety, Obstet. Gynecol. 97:873-79, 2001.

Brochure, "GPS for Pelvic Floor Repair," Gynecare Prolift, 6 pages, 2005.

\* cited by examiner or

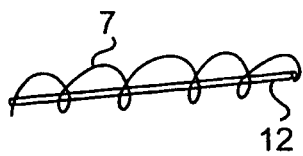
Fig. 6A
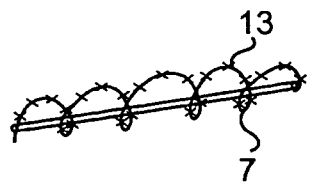
Fig. 6B
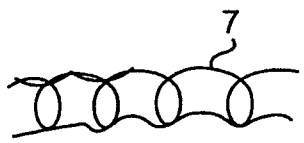
Fig. 6C
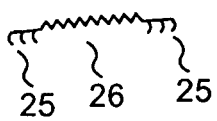          
Fig. 6D            Fig. 6E            Fig. 6F

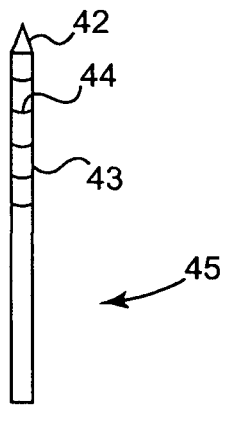
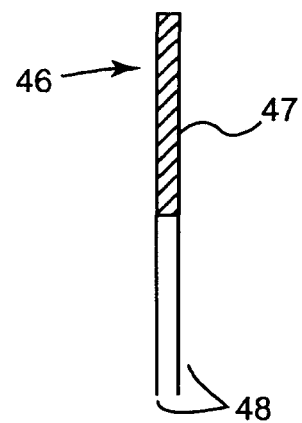
Fig. 14      Fig. 15
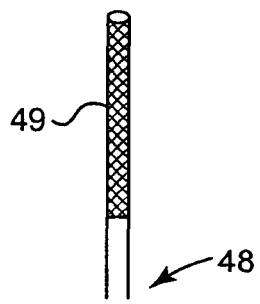
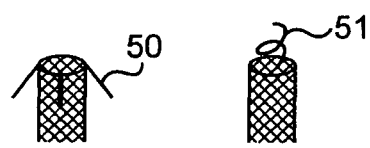
Fig. 15A      Fig. 16
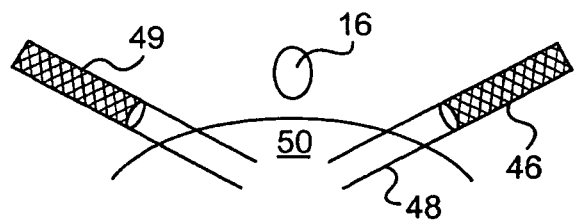
Fig. 17
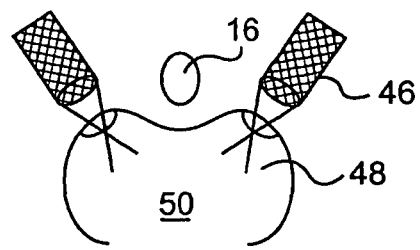
Fig. 18

METHOD AND ARTICLES FOR TREATMENT OF STRESS URINARY INCONTINENCE

PRIORITY

This application claims benefit from International Application No. PCT/US2007/069370, having PCT Publication No. WO 2007/137226, which was filed on 21 May 2007, which in turn claims priority under 35 USC §119(e) to U.S. Provisional Application Ser. No. 60/747,736, filed 19 May 2006 and to U.S. Provisional Application Ser. No. 60/819,370, filed 10 Jul. 2006, the entire content of each application being incorporated herein by reference.

BACKGROUND OF THE INVENTION

1. Field of the Invention

This invention relates to urogenital medicine and surgery.

2. Description of the Related Art

Over 13 million American men and women of all ages suffer from urinary incontinence. The social implications for an incontinent patient include loss of self-esteem, embarrassment, restriction of social and sexual activities, isolation, depression and, in some instances, dependence on caregivers. Incontinence is the most common reason for institutionalization of the elderly.

The urinary system consists of the kidneys, ureters, bladder and urethra. The bladder is a hollow, muscular, balloon-shaped sac that serves as a storage container for urine. The bladder is located behind the pubic bone and is protected by the pelvis. Ligaments hold the bladder in place and connect it to the pelvis and other tissue. FIG. 1 schematically illustrates female anatomy. The urethra 16 is the tube that passes urine from the bladder 14 out of the body. The narrow, internal opening of the urethra 16 within the bladder 14 is the bladder neck 18. In this region, the bladder's bundled muscular fibers transition into a sphincteric striated muscle called the internal sphincter. FIG. 2 schematically illustrates male anatomy. The urethra 16 extends from the bladder neck 18 to the end of the penis 22. The male urethra 16 is composed of three portions: the prostatic, bulbar and pendulus portions. The prostatic portion is the widest part of the tube, which passes through the prostate gland 24.

Incontinence may occur when the muscles of the urinary system malfunction or are weakened. Other factors, such as trauma to the urethral area, neurological injury, hormonal imbalance or medication side-effects, may also cause or contribute to incontinence. There are five basic types of incontinence: stress incontinence, urge incontinence, mixed incontinence, overflow incontinence, and functional incontinence. Stress urinary incontinence (SUI) is the involuntary loss of urine that occurs due to sudden increases in intra-abdominal pressure resulting from activities such as coughing, sneezing, lifting, straining, exercise and, in severe cases, even simply changing body position. Urge incontinence, also termed "hyperactive bladder" "frequency/urgency syndrome" or "irritable bladder," occurs when an individual experiences the immediate need to urinate and loses bladder control before reaching the toilet. Mixed incontinence is the most common form of urinary incontinence. Inappropriate bladder contractions and weakened sphincter muscles usually cause this type of incontinence. Mixed incontinence is a combination of the symptoms for both stress and urge incontinence. Overflow incontinence is a constant dripping or leakage of urine caused by an overfilled bladder. Functional incontinence results when a person has difficulty moving from one place to another. It is generally caused by factors outside the lower urinary tract, such as deficits in physical function and/or cognitive function.

Stress urinary incontinence is generally thought to be related to hypermobility of the bladder neck or an intrinsic urethral sphincter defect.

A variety of treatment options are currently available to treat incontinence. Some of these treatment options include external devices, behavioral therapy (such as biofeedback, electrical stimulation, or Kegal exercises), injectable materials, prosthetic devices and/or surgery. Depending on age, medical condition, and personal preference, surgical procedures can be used to completely restore continence.

Conservative management of stress urinary incontinence can include lifestyle changes, such as weight loss, smoking cessation, and modification of intake of diuretic fluids such as coffee and alcohol. With regard to surgical treatments, the purported "gold standard" is the Burch Colposuspension, in which the bladder neck is suspended. Mid-urethral slings have been similarly effective. One type of procedure, found to be an especially successful treatment option for SUI in both men and women, is a sling procedure.

A sling procedure is a surgical method involving the placement of a sling to stabilize or support the bladder neck or urethra. There are a variety of different sling procedures. Slings used for pubovaginal procedures differ in the type of material and anchoring methods. In some cases, the sling is placed under the bladder neck and secured via suspension sutures to a point of attachment (e.g. bone) through an abdominal and/or vaginal incision. Examples of sling procedures are disclosed in U.S. Pat. Nos. 5,112,344; 5,611,515; 5,842,478; 5,860,425; 5,899,909; 6,039,686; 6,042,534, 6,110,101, and 6,652,450, all of which are herein incorporated by reference.

Although serious complications associated with sling procedures are infrequent, they do occur. Complications include urethral obstruction, development of de novo urge incontinence, hemorrhage, prolonged urinary retention, infection, and damage to surrounding tissue and sling erosion.

As noted above, injectable materials are an option for treatment of stress urinary incontinence. These have generally consisted of the injection of bulking agents into tissues surrounding the urethra to allow these tissues to better support the urethra, and help the urethral sphincter function properly. Collagen is sometimes used. Carbon coated beads are also used. Certain polymers have also been used. All of these injectable agents have the disadvantage of requiring multiple repeated treatments to maintain efficacy.

Prolotherapy is a technique wherein sclerosing substances, such as dextrose, are injected into musculosketal structures to induce changes in the ligaments and tendons due to increased proliferation of the tissue. This technique is also used in treatment of ocular conditions. In these techniques, the substance is injected. This leads to localized inflammation, which leads to the wound healing process. This results in a deposition of new collagen, which shrinks as it heals. The shrinking collagen tightens the ligaments. These techniques have not been applied to urologic disorders. These techniques are further described *Ligament and Tendon Relaxation Treated by Prolotherapy*, by George S. Hackett, which is herein incorporated by reference in its entirety.

There is a desire for a minimally invasive yet highly effective treatment modality that can be used with minimal to no side effects. Such a modality should reduce the complexity of a treatment procedure, be biocompatible, should reduce pain, operative risks, infections and post operative hospital stays, and have a good duration of activity. Further, the method of treatment should also improve the quality of life for patients.

SUMMARY OF THE INVENTION

The present invention includes surgical instruments, implantable articles, and methods for urological applications, particularly for the treatment of stress and/or urge urinary incontinence, fecal incontinence, and prolapse and perineal floor repairs.

As noted, the usual treatments for stress urinary incontinence include placing a sling to either compress the urethral sphincter or to elevate or support the neck of the bladder defects. In the present invention, hypermobility in the female or male stress urinary incontinence patient is treated by use of a neoligament.

For purposes of the present invention, the term neoligament is used to describe a synthetic, tissue, or composite tissue/synthetic structure that has the fixation, stiffness, and strength required to support the urethra, rectum, or pelvic floor muscles during a stress event such that the symptoms of stress urinary or fecal incontinence are reduced or eliminated.

In the present invention, a neoligament is formed from any suitable material, for example, any suitable polymeric product, such as expanded polytetrafluoroethylene, polypropylene, polyethylene terephthalate, or polycarbonate urethane, hydrogel, or a resorbable or nonresorbable biological material. The neoligament may be formed into any suitable configuration, for example, a knitted, woven, braided, barbed, tubular, or stent-like configuration.

The present invention also includes several methods for use of a neoligament for treating aeveral pelvic conditions including, but not limited to, stress and/or urge urinary incontinence and fecal incontinence, and pelvic or perineal floor repairs in both male and female patients. One preferred embodiment includes placing the formed neoligament device or element into its selected location through a tube, needle, or similar deployment device into the obturator internus, obturator membrane, space of retzius, endopelvic fascia and/or perineal floor. Another preferred method comprises forming the neoligament in situ. This method includes steps of injecting a fibrosing agent through a tube, needle, or other suitable device into the obturator internus, obturator membrane, space of retzius, endopelvic fascia and/or perineal floor. The fibrosing agent may be in the form of a liquid, gel, foam, solid, or a solution containing the fibrosing agent. The fibrosing agent can be any suitable agent.

The present invention also encompasses a self-tensioning elastic tissue bolster which can be, similar to the neoligament, implanted into the tissues that support the urethra, bladder, rectum, pelvic, or perineal floor. Similar to the neoligament, such a tissue bolster has the advantage of requiring minimal surgery, thus being amenable to in-office outpatient implantation. Such bolster implants would have efficacy similar to sling treatment of stress incontinence. However, the device is made to be of such a small size that it can be implanted through a small incision or puncture, with minimal bleeding, pain, and complications.

The present invention also encompasses a method of treating various forms of incontinence or effecting pelvic floor repair by using an injectable agent to shrink the collagen in the ligaments and other tissues that support the urethra, bladder, rectum, and pelvic floor. Further, such injections can be used to alter the collagen in the urethra, as such a change in collagen structure may increase the resistance to urine flow through the urethra, or to correct the ano-rectal angle for fecal incontinence. Such treatment is minimally invasive and is a targeted treatment with minimal adverse side effects.

The present invention also encompasses transvaginal or transperineal urethral bolster systems.

The present invention also encompasses bladder or rectal pillar systems.

While reference is made to use of the disclosed neoligament, tissue bolster devices, and collagen alteration methods for treatment of stress urinary incontinence, it is clear that such techniques and devices are equally applicable to treatment of pelvic organ prolapse conditions, such as cystocele and rectocele. Further, such methods may be adaptable to treatment of fecal incontinence. Accordingly, such treatments are within the scope of the present invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 6A shows another embodiment of the self-tensioning elastic tissue bolster.

FIG. 6B shows another embodiment of the self-tensioning elastic tissue bolster.

FIG. 6C shows another embodiment of the self-tensioning elastic tissue bolster.

FIG. 6D shows another embodiment of the self-tensioning elastic tissue bolster.

FIG. 6E shows another embodiment of the self-tensioning elastic tissue bolster.

FIG. 6F shows another embodiment of the self-tensioning elastic tissue bolster.

FIG. 14 shows an embodiment of the transvaginal urethral bolster needle introducer.

FIG. 15 shows an embodiment of the transvaginal urethral bolster.

FIG. 15A shows an embodiment of the transvaginal urethral bolster.

FIG. 16 shows modifications of the transvaginal urethral bolster.

FIG. 17 shows the transvaginal urethral bolster in place.

FIG. 18 shows the transvaginal urethral bolster in place.

DETAILED DESCRIPTION OF THE PREFERRED EMBODIMENTS

Figure 1:
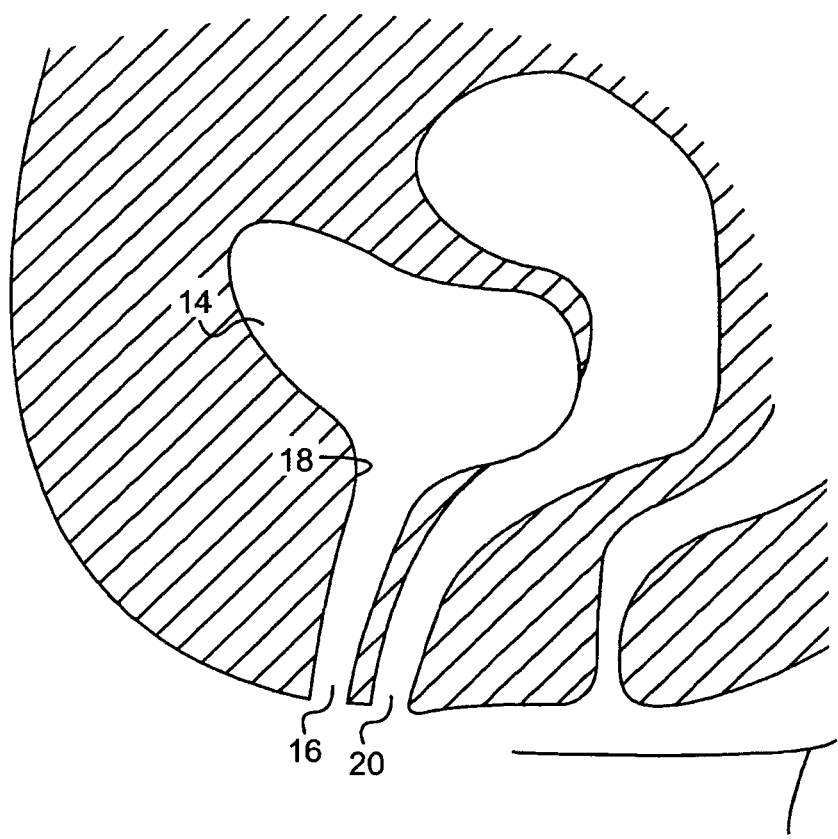
FIG. 1 shows a schematic view of the female urinary system.
Figure 2:
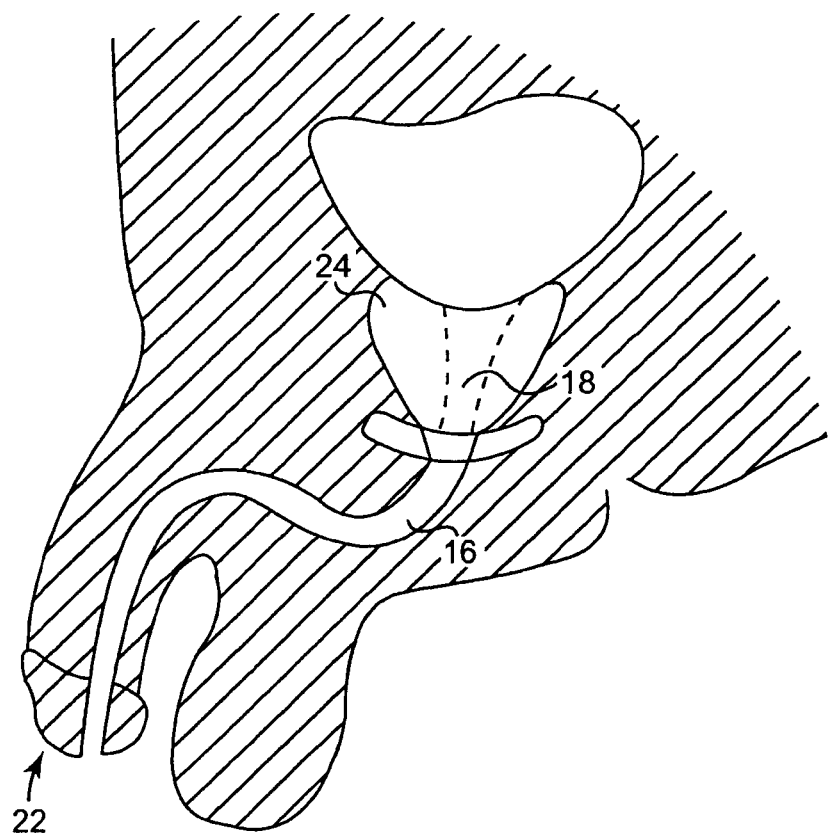
FIG. 2 is a schematic view of the male urinary system.

Referring now to the drawings, wherein like reference numerals designate identical or corresponding parts throughout the several views. The following description is meant to be illustrative only, and not limiting other embodiments of this invention will be apparent to those of ordinary skill in the art in view of this description.

One aspect of the present invention is a pessary-like device which is used to hold the anterior vaginal wall and tissues deep to the vaginal wall in proper position during the formation of the neoligament. The pessary-like device may be, as clinically appropriate, adjustable. It may be formed to act primarily on the vaginal wall under the urethra, or it may act primarily on the vaginal wall lateral to the urethra. The pessary-like device may be made from a material including inhibizone, antimicrobial, and or antifungal agents. Further, an adjustable pessary-like device may be adjustable via inflation or deflation of a cuff or bladder in the device. Further, an adjustable pessary-like device may be lengthened or shortened in one direction by inflation or deflation of a cuff or a cylinder that is turned inside-out onto itself. Further, the pessary-like device may have one or more ports through it for injection of fibrosing agents or placement of a neoligament. Such ports would preferably be placed at such locations to approach the target areas, including the obturator internus, obturator membrane, space of retzius, perineal floor, rectum, and/or endopelvic fascia. The pessary-like device can optionally include a through hole or aperture so as to not occlude the vaginal canal when the device is in place.

Another aspect of the present invention is a specialized needle, trocar, introducer, syringe, or tube for placing a formed neoligament or a fibrosing agent. Among preferred embodiments are articulating needles, syringes, or tubes for directing the neoligament or fibrosing agent to the desired target tissue. A preferred embodiment is a curved needle, syringe, or tube. Another preferred embodiment is a needle, tube, or syringe formed of elastic or super elastic material that curves toward target tissues as it is advanced from a straight introducer.

Figure 3B:
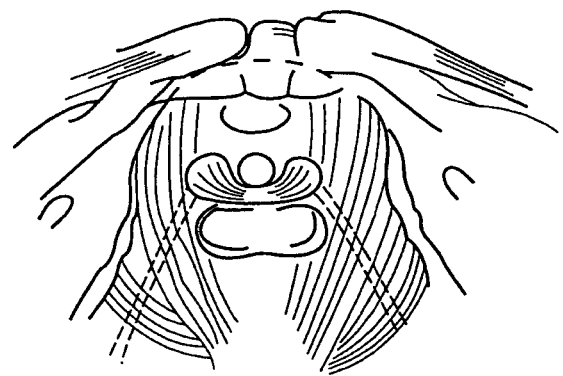
FIGS. 3A and 3B are views of the injection of fibrosing agent to form a neoligament.
Figure 3A:
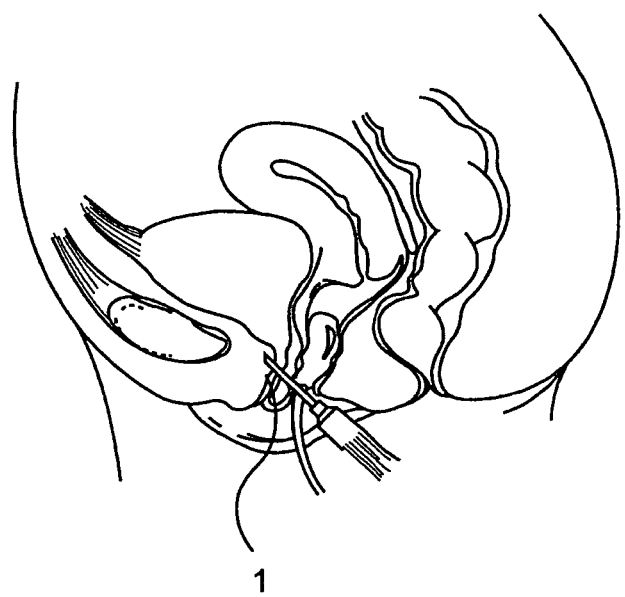

Another aspect of the present invention is the method of treating stress urinary incontinence using a neoligament formed in situ, as seen in FIG. 3. The method comprises arranging the anterior vaginal wall and tissues deep to the vaginal wall in proper position for the formation of the neoligament. The method includes a transvaginal or transperineal injection, and may optionally include use of local anesthesia. A needle, tube, or syringe is used to inject a fibrosing agent into the anterior vaginal wall (or pelvic floor for males), lateral to mid-urethra, and or bladder neck (illustrated as member 1 in FIG. 3), as needed. The fibrosing agent causes fibrosis in the tissue, resulting in a neoligament for suspension of the anterior vaginal wall and the urethra.

Figure 4B:
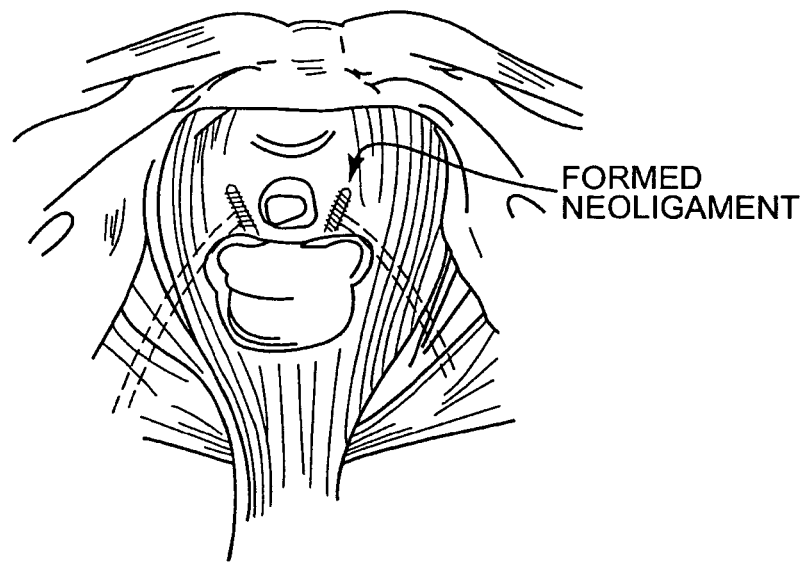
FIGS. 4A and 4B are views of the introduction of a formed neoligament into its proper location.
Figure 4A:
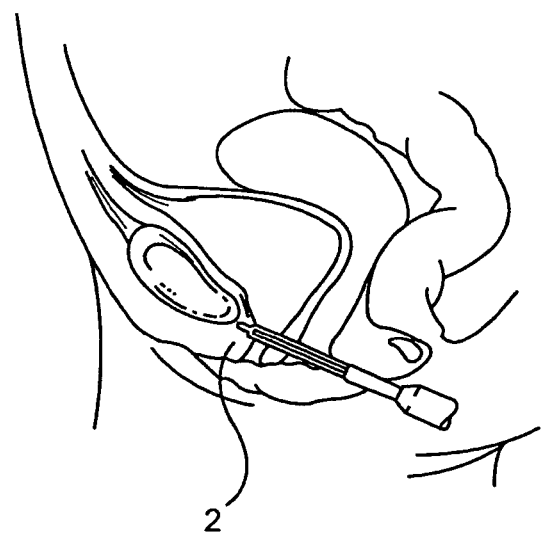

Another aspect of the present invention is the method of treating stress urinary incontinence using a neoligament formed prior to the procedure, as seen in FIG. 4. This method differs from the in situ method in that a neoligament is implanted into the target tissue. Such a neoligament may be formed in any conventional method of manufacturing medical implants. This method may also use a transvaginal or transperineal approach. Local anesthetic may be injected into the anterior vaginal wall in the female. The formed neoligament is placed via an appropriate implantation device into the anterior vaginal wall (or pelvic floor for males), lateral to mid-urethra, or bladder neck (illustrated as member 2 in FIG. 4), on both sides, in order to effect a bolstering or suspension effect of the anterior wall of the vagina.

Figure 5A:
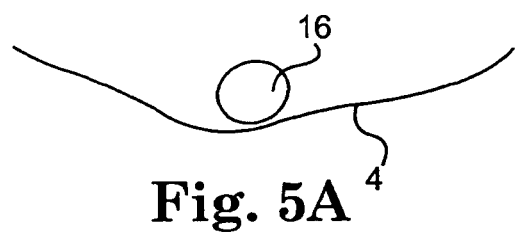
FIG. 5A shows the lax tissue causing hypermobility of the urethra.

Another aspect of the present invention is a self-tensioning elastic tissue bolster. An embodiment of the self-tensioning elastic tissue bolster of the present invention may include a small spring or elastic component that can be implanted into the tissues that support the urethra or bladder neck. In a related embodiment, the spring or stent-like element includes tissue anchors at one or both ends to pull the surrounding tissues in as the spring compresses so as to tighten the area around the urethra, rectum, or pelvic floor. In other embodiments, a material other than a spring, such as a suitably elastic fabric or polymer material, may be used to form the tissue bolster. The tissue bolsters serve to increase the support provided by the lax support structures, as such laxity contributes to incontinence, as illustrated schematically in FIG. 5A, where member 16 is the urethra or bladder neck and member 4 is the lax support structure.

Figure 5B:
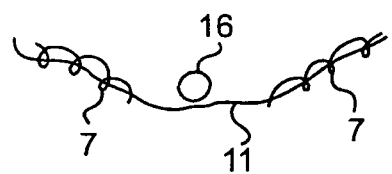
FIG. 5B shows the self-tensioning elastic tissue bolster with the springs relaxed.
Figure 5C:
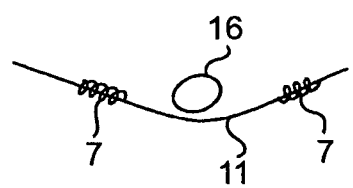
FIG. 5C shows the self-tensioning elastic tissue bolster with the springs elongated.
Figure 5D:
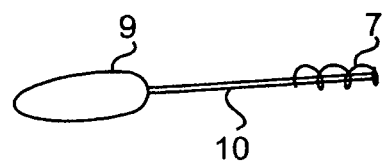
FIG. 5D shows a tool for implantation of the self-tensioning elastic tissue bolster.
Figure 5E:
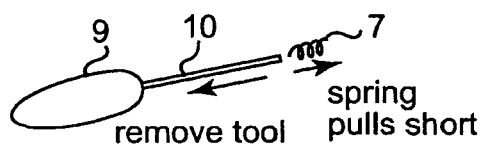
FIG. 5E shows another aspect of a tool for implantation of the self-tensioning elastic tissue bolster.
Figure 5F:
FIG. 5F shows an embodiment of the self-tensioning elastic tissue bolster.
Figure 5G:
FIG. 5G shows another embodiment of the self-tensioning elastic tissue bolster.

The elastic or spring component of the present invention may be implanted in an elongated state, as illustrated in FIG. 5B, in which the implant is illustrated by member 11. After anchoring the two ends of the implant in tissue by, for example, using tissue anchors as shown in FIGS. 5F and 5G, the elastic or spring component 7 is allowed to contract to its natural state, shortening the implant and resulting in increased support to the urethra and bladder neck, as illustrated in FIG. 5C. In addition to supporting the urethra and bladder neck by increasing the tension in the support tissues, the implant of the present invention also increases the strength of those support tissues by the integration of the implant itself into the tissues and by the tissue healing response initiated by the foreign body reaction, resulting in remodeling of the support tissues. This strengthening function can also be used to address fecal and urge incontinence as well as to simplify pelvic floor and vaginal repairs that can be performed in an office setting.

With regard to the tissue anchors, the present invention encompasses any suitable anchor structures. Without limitation, FIG. 5F illustrates an embodiment having anchor structures 5 and 6 attached to one or both ends of the spring or elastic component 7. The spring or elastic component may further include additional grip structure. In a preferred embodiment, the spring or elastic structure may be provided within a covering structure 8 with attached anchors, as illustrated in a non-limiting example in FIG. 5G.

Figure 9A:
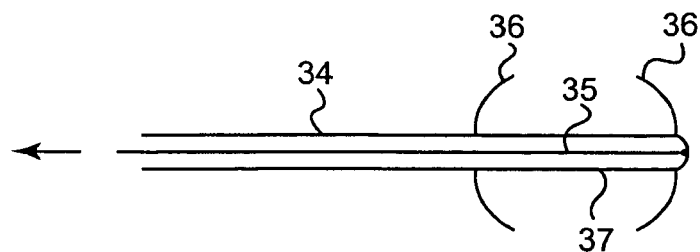
FIG. 9A-9C show another embodiment of the tool for implantation of the self-tensioning elastic tissue bolster.
Figure 9B:
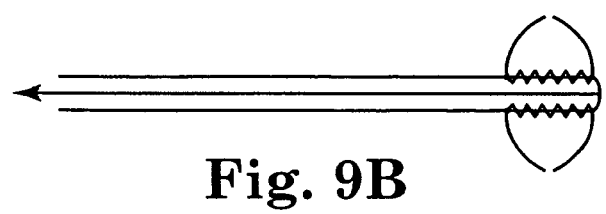
Figure 9C:
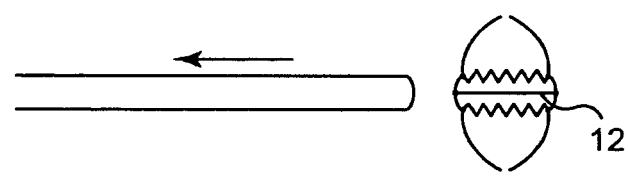
Figure 9D:
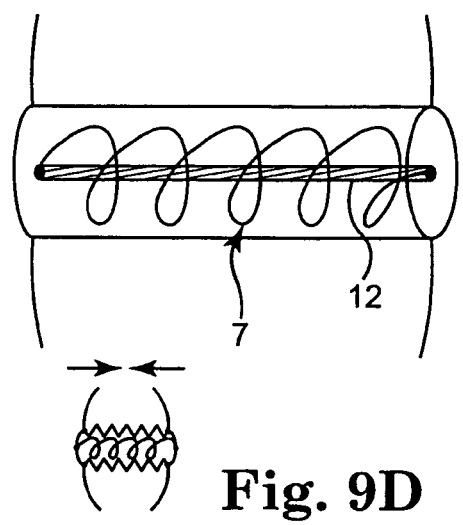
FIG. 9D shows another embodiment of the self-tensioning elastic tissue bolster.

In a further embodiment of the tissue bolster of the present invention, the elastic material is held in its elongated position by a bioabsorbable brace after implant into the supporting tissues, as shown in FIGS. 6A, 9D, and 10. Such a brace, illustrated as member 12, allows the body of the patient to heal in such a way that tissue in-growth into the implant occurs. After sufficient period to allow such in-growth to affect an anchor to the ends of the implant (approximately 1 week to 1 month), the brace is absorbed or otherwise removed, at which time the spring contracts to its natural position, resulting in tension in the supporting tissues and support of the urethra or bladder neck. Similarly, the implant of the present invention may be coated or wrapped in a material that promotes such in-growth of tissue, as shown in FIG. 6B, illustrated as member 13. The growth promoting material may be any such material, including a mesh, a drug coating, or a plastic. The spring or elastic material could be wrapped in fabric, as shown in FIG. 6C, illustrated as member 15.

Figure 10A:
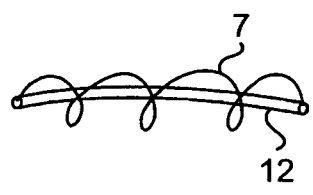
FIG. 10A-10C show another embodiment of the self-tensioning elastic tissue bolster.
Figure 10B:
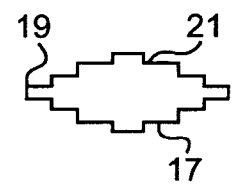
Figure 10C:
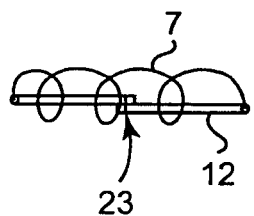

In a further embodiment, the bioabsorbable brace holding the implant in its elongated state can be built such that it gradually weakens, resulting in more gradual application of the increased tension in the tissues. Such a gradual increase in tension would likely result in less risk of tearing or pain. This can be affected by providing the bioabsorbable brace 12 in a flexed position, such that the brace flexes more as it weakens, as seen in FIG. 10A. In an alternative embodiment, the bioabsorbable brace can be provided in a capsule with differing kinds or amounts of bioabsorbable material placed in different locations on the brace. The brace capsule could, for example, selectively absorb on the ends of the capsule before absorbing more toward the center of the brace, allowing gradual contraction of the elastic device, as shown in FIG. 10B, with member 17 representing the capsule, member 19 representing the portions of the capsule that absorb most quickly, and member 21 representing the portions of the capsule that absorb most slowly. Likewise, in a further embodiment, a bioabsorbable suture could be used to deploy the elastic device in its elongated state, with the elastic device contracting upon absorption of the suture, as shown in FIG. 10C, with the suture illustrated as member 23.

Figure 7A:
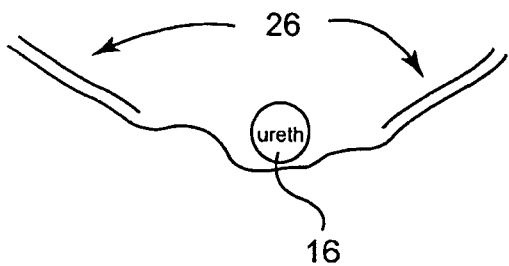
FIG. 7A shows another embodiment of the self-tensioning elastic tissue bolster.
Figure 7B:
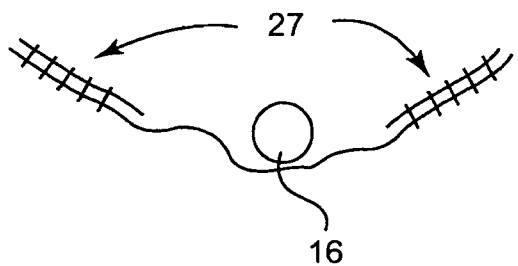
FIG. 7B shows another embodiment of the self-tensioning elastic tissue bolster.
Figure 7C:
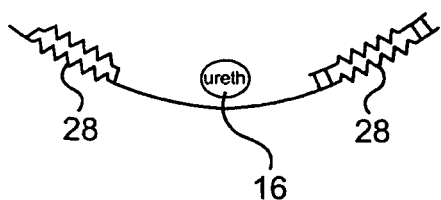
FIG. 7C shows another embodiment of the self-tensioning elastic tissue bolster.

In another embodiment of the present tissue bolster implant, the implant may be an elastic cloth or polymer. FIG. 6D illustrates an example of such an implant, wherein the elastic implant may be implanted with tissue hooks or anchors 25 to allow initial attachment, followed by contraction of the elastic material 26 or spring or stent-like member, pulling the tissue to which the hooks or anchors are attached more closely together, as shown in FIG. 6E. In another embodiment, the implant may be of an elastic material in which tissue in-growth is encouraged. In a related embodiment, as the tissue grows into the elastic material, the elastic and the in-grown material are stretched concurrently, as shown in FIG. 6F, resulting in increased tension in the supporting structure and better support of the urethra, bladder neck, or rectum. Such an embodiment is shown in FIGS. 7A, 7B, and 7C. Member 26 represents the stretched elastic implant, member 27 represents the tissue ingrowth into the elastic implant, and member 28 represents the contracted elastic with ingrown tissue, in its tightened condition.

In a further embodiment of the tissue bolster of the present invention, the implant may further include a mechanism that can contract the implant and tension the tissue an adjustable degree as determined by the physician at the time of implantation. Such an embodiment may include a spring with tissue anchors at each end.

Figure 7D:
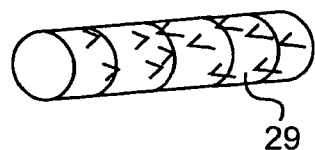
FIG. 7D shows another embodiment of the self-tensioning elastic tissue bolster.

In a further embodiment, the implant elastic material of the present invention includes a spring or elastic material surrounded by a cloth or polymer coating that is coated with tissue anchors 29, as shown in FIG. 7D.

The present invention also encompasses a tool for implanting the implant of the present invention. The tool may be of any design suitable for holding the spring or elastic component in an elongated condition until removal of the tool, at which time the spring or elastic component contracts to its more natural condition. An example of such a tool is illustrated in FIGS. 5D (with the implant elongated) and 5E (with the implant contracted following removal of the tool). The tool may include a handle 9 and an insertion structure 10.

Figure 7E:
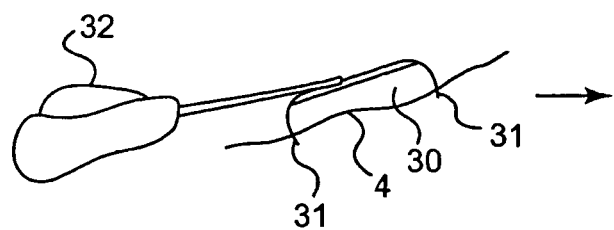
FIGS. 7E-7F show another embodiment of the tool for implantation of the self-tensioning elastic tissue bolster.
Figure 7F:
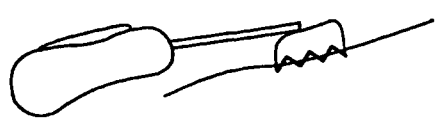

In another embodiment, the implantation tool includes features for the manual adjustment of the tension in the implant during the implantation procedure. Such features may include features illustrated in FIGS. 7E and 7F. This type of implantation tool may be effectively used to place a non-elastic or non-spring implant, as the implant material can be tensioned manually by the operator. For example, FIG. 7E illustrates an implant 30 having hooks or anchors 31 that are engaged in the lax tissue. By engaging a squeeze device 32 on the handle, the implant is contracted, pulling the engaged tissue points more closely together, and tensioning the lax tissue. Other related implant tools are illustrated in U.S. Patent Publication 2002/0161382 and 2004/0039453, which are herein incorporated by reference in their entirety.

Figure 8A:
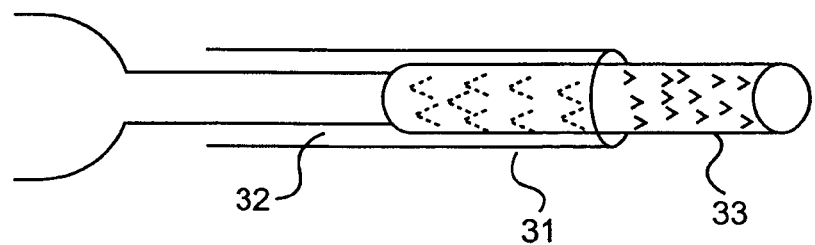
FIG. 8A-8C show another embodiment of the tool for implantation of the self-tensioning elastic tissue bolster.
Figure 8B:
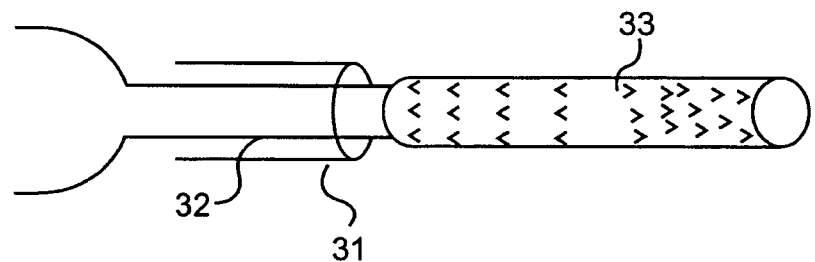
Figure 8C:
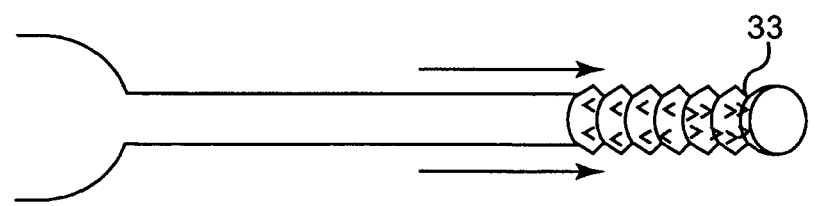

In a further embodiment of an implantation tool, the tool may include a handle and an insertion structure for holding the elastic device in an elongated state while inserting it. FIGS. 8A-C illustrate an embodiment of an implantation tool for implanting an elastic implant device having tissue anchors covering the implant 33. The implantation tool may include a sheath 31 to cover such anchors during implantation, as shown in FIGS. 8A-8C. The implantation tool may further include a mechanism 32 for placing the implant 33. When actuated, the mechanism 32 places the implant, and the sheath 31 is withdrawn. The implant is contracted, pulling the tissue together at the ends of the implant. This is further facilitated by having tissue anchors disposed in opposite directions on opposite ends of the implant. Tension in the lax supporting tissues is thus increased.

As illustrated in a non-limiting example in FIGS. 9A-9C, a further embodiment of an implantation tool may include a detachable handle 34, a mechanism for holding the implantable elastic device in an elongated state 35, and relatively long anchors 36 proximal and distal to the elongated elastic or spring device 37. The mechanism 35 can actuate the anchors, such as by pulling the anchors together, as shown in FIGS. 9A-9C. The elongated device is placed in the appropriate location such that the hooks on each side of the elongated device engage tissue requiring further tension. When the tissue is engaged by the hooks, the anchors are actuated, pulling the anchors together, and allowing for contraction of the elastic device and increased tension in the engaged tissue. Upon actuation of the anchors, the implantation tool handle is detached from the implanted elastic device and the handle is removed.

Another aspect of the present invention is a method of treating stress urinary incontinence using prolotherapy. An injectable agent is used to shrink the collagen in the ligaments and other tissues that support the urethra, bladder, and pelvic floor. Further, such injections can be used to alter the collagen in the urethra, as such a change in collagen structure may increase the resistance to urine flow through the urethra.

Figure 11:
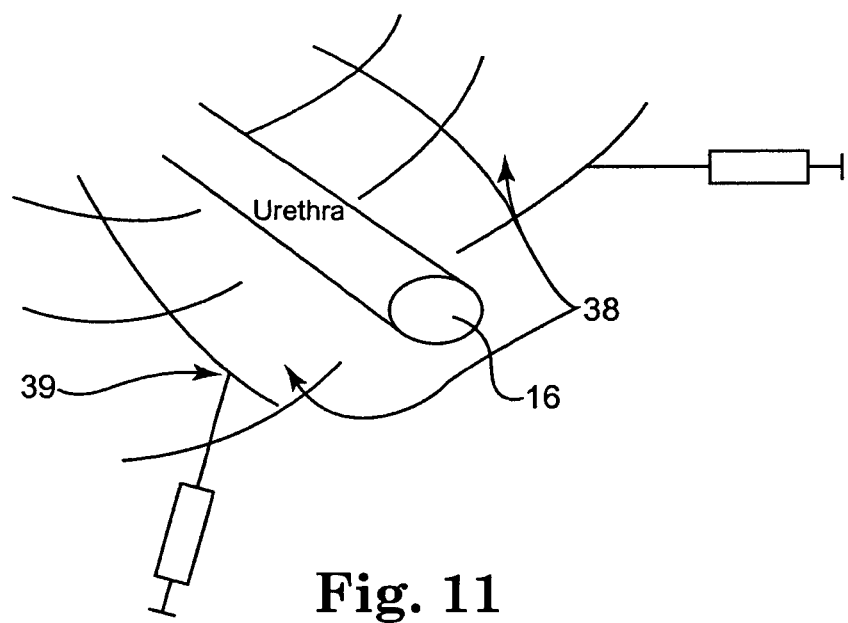
FIG. 11 shows an embodiment of the method of treating incontinence by prolotherapy.

In an embodiment of the present invention, an injectable agent is injected into the tissues that support the urethra, indicated by member 39 in FIG. 11, or bladder neck. The injectable agent may include one or more of saline, dextrose, and other known proliferation agents (which include phenol, glycerine, and morrhuate sodium). Any suitable and appropriate supportive tissue is amenable to such injection, including pubocervical fascia, as shown in FIG. 11, and indicated by member 38. Other preferred locations include the pubourethral ligament, the lateral pubovesical ligament, the arcus tendon of the levator ani muscle, in and about the puborectalis muscle, and the perineal floor. The injections result in a healing process wherein collagen is formed. As the newly formed collagen shrinks, the injected structure tightens, thereby improving in its supportive function.

Figure 12:
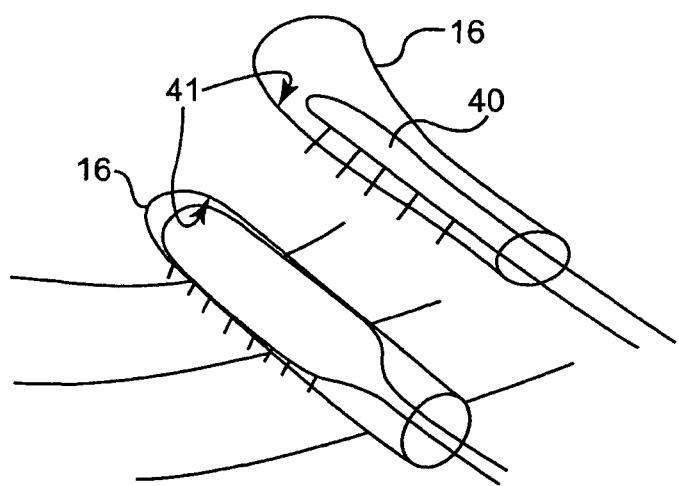
FIG. 12 shows another embodiment of the method of treating incontinence by prolotherapy.
Figure 13A:
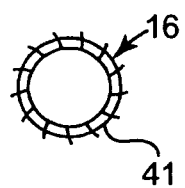
FIG. 13 shows another embodiment of the method of treating incontinence by prolotherapy.
Figure 13B:
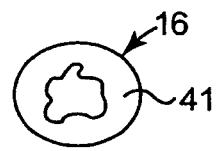

In another embodiment, the injectable agents described are injected into the urethra, as in the posterior wall of the urethra shown in FIG. 12. This injection is facilitated by use of small needles that cannot pierce the urethra and enter the lumen of the organ. Further, the invention includes inserting a balloon or other inflatable marking device 40 into the urethra 16, then inflating the balloon, as illustrated in FIG. 12. Following such inflation, the injectable agents can easily be injected into the wall 41 of the urethra without penetrating the lumen. Injection into all sides of the tubular organ is shown in FIG. 13A, with the thickened wall post-therapy illustrated in FIG. 13B.

The present invention also encompasses a transvaginal or transperineal urethral, rectal, or pelvic floor bolster system. This system includes a needle introducer 45, a non-limiting example of which is illustrated in FIG. 14, and may include an elongated needle 42 with a hollow sheath 43. Optionally, markings 44 on the sheath indicate depth of placement. Other methods of indicating depth of placement also fall within the scope of the present invention. The system also includes a bolster, a non-limiting example of which is illustrated in FIG. 15. The bolster 46 may be wrapped and compressed in a plastic covering 47, and is dimensioned to be placed through the introducer. The bolster is preferably formed of a mesh material. The bolster includes sutures 48 on each end. The bolster may preferably include a high friction surface, indicated by member 49 in FIG. 15. The bolster may include anchoring structures, examples of which are illustrated in FIG. 16, including barbs 50 or corkscrews 51. Other anchoring structures are also within the scope of the present invention.

The present invention also encompasses a method of treating urinary stress or urge incontinence by use of transvaginal urethral bolsters. The method includes local anesthesia infiltration into the paravaginal fascia at the midurethral level, towards the urogenital diaphragm. Following such infiltration, a needle introducer is inserted. The needle is removed, leaving the sheath in place. A bolster is inserted through the sheath. The sheath of the introducer is withdrawn, and the mesh material in the bolster is released. The mesh material expands and is held in place by friction or by anchoring structures. As illustrated in FIG. 17, the bolsters 46 are placed with the sutures extending into the vagina 50. The sutures connected to the mesh material are tied in the vagina over a bolster that compresses the vagina toward the urogenital diaphragm, as illustrated in FIG. 18. This tightens the paravaginal fascia and reduces urethral hypermobility. The amount of tension can be adjusted to prevent urethral obstruction. As the paravaginal fascia grows into the mesh, the urethra is stabilized. After tissue ingrowth, the sutures in the vagina are cut.

Figure 23:
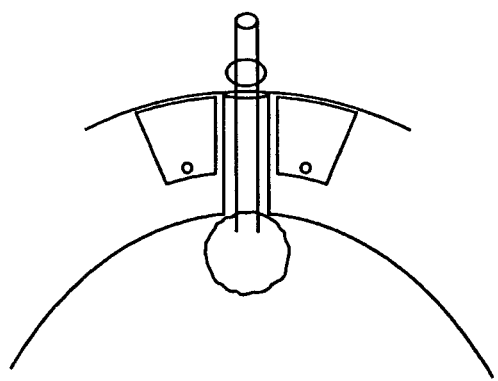
FIG. 23 is an overview of the bladder pillar system.

The present invention also encompasses bladder pillars. These pillars provide lateral urethral support and induce new collagen growth. The surgeon identifies the mid-urethra area, which has the greatest urethral pressure, and places a pillar through the vaginal mucosa into the paravaginal fascia to support this region of the urethra. FIG. 23 shows the schematic placement of bladder pillars.

Figure 19:
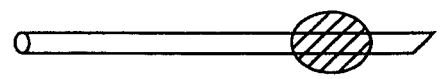
FIG. 19 shows the urethral guide for the bladder pillar system.

The bladder pillar system requires identification of the mid-urethra area in order to effect proper placement. The present invention encompasses a urethral guide/template for such identification. An example is illustrated in FIG. 19. The urethral guide may include indicia to allow location of the correct placement.

Figure 20:
FIG. 20 shows a coiled embodiment of the bladder pillar.

The bladder pillar may be of several different configurations. FIG. 20 shows an embodiment in which the pillar is coiled. Such a coiled pillar 51 may be placed by screwing into place, compressing the tissue as it is advanced.

Figure 21:
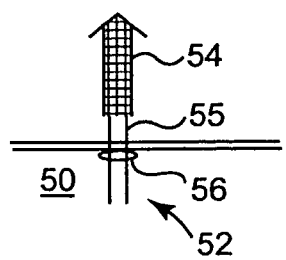
FIG. 21 shows an adjustable embodiment of the bladder pillar.

The bladder pillar may be adjustable. FIG. 21 illustrates an example of such an adjustable pillar. The adjustable pillar 52 may include a self-anchoring tip 53. The body 54 of the pillar may optionally include prolene or may be absorbable. Sutures 55 for adjusting the length of the body of the pillar extend into the vagina following placement. An adjustable slip button 56 is situated on the vaginal side to adjust the tension and hold the pillar in place until tissue in-growth has occurred.

Figure 22:
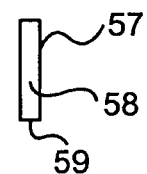
FIG. 22 shows an expandable embodiment of the bladder pillar.

The bladder pillar may also be expandable. FIG. 22 illustrates an example of an expandable pillar. The expandable pillar 60 includes a probe 57 with an expandable side 58 located toward the urethra. The pillar can be inflated through an injection site 59 with saline to exert lateral pressure on the urethra. Adding or removing saline can be used to adjust the pressure over time.

Numerous modifications and variations of the present invention are possible in light of the above teachings. Further, these techniques and devices are described as treatment for urinary incontinence. Their use in treating organ prolapse and other urologic conditions is also contemplated. It is therefore to be understood that within the scope of the appended claims, the invention may be practiced otherwise than as specifically described herein.

The invention claimed is:

1. A method of treating urinary incontinence comprising injecting a proliferative agent in supportive tissue that supports a tissue selected from the group consisting of: a urethra, bladder, and pelvic floor tissue;
   wherein the proliferative agent results in shrinkage of collagen of the supportive tissue, which treats the urinary incontinence.

2. The method of claim 1, comprising injecting the proliferative agent into a wall of the urethra.

3. The method of claim 2 wherein the step of injecting the proliferative agent into a wall of the urethra comprises injecting the proliferative agent into a wall of the urethra using a plurality of small needles.

4. The method of claim 3 wherein the proliferative agent is injected around all sides of and into the wall of the urethra using the plurality of small needles.

5. The method of claim 2, further comprising introduction of an inflatable marking device into the urethra to identify the walls of the urethra.

6. The method of claim 1, wherein said proliferative agent is selected from the group including saline, dextrose, phenol, glycerine, and morrhuate sodium.

7. The method of claim 1, wherein said proliferative agent is selected from the group including dextrose, phenol, glycerine, and morrhuate sodium.

8. A method of claim 1 wherein the supportive tissue is selected from the group consisting of: pubocervical fascia, a pubourethral ligament, a lateral pubovesical ligament, an arcus tendon of a levator ani muscle, and a perineal floor.

* * * * *